US008080235B2

United States Patent
Zhang et al.

(10) Patent No.: US 8,080,235 B2
(45) Date of Patent: Dec. 20, 2011

(54) PROTEIN KINASE A REPORTERS USEFUL IN HIGH THROUGHPUT ASSAYS

(75) Inventors: Jin Zhang, Baltimore, MD (US); Qiang Ni, Baltimore, MD (US); Michael David Allen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 643 days.

(21) Appl. No.: 12/091,858

(22) PCT Filed: Oct. 26, 2006

(86) PCT No.: PCT/US2006/041741
§ 371 (c)(1),
(2), (4) Date: Nov. 18, 2008

(87) PCT Pub. No.: WO2007/050734
PCT Pub. Date: May 3, 2007

(65) Prior Publication Data
US 2009/0317333 A1    Dec. 24, 2009

Related U.S. Application Data

(60) Provisional application No. 60/800,451, filed on May 15, 2006, provisional application No. 60/730,750, filed on Oct. 27, 2005.

(51) Int. Cl.
*G01N 33/52* (2006.01)
*G01N 33/533* (2006.01)
*G01N 33/542* (2006.01)
*A61K 38/00* (2006.01)

(52) U.S. Cl. .......... 424/9.6; 424/52; 536/26.6; 436/546; 436/800

(58) Field of Classification Search .................. None
See application file for complete search history.

(56) References Cited

FOREIGN PATENT DOCUMENTS
WO    2005036178 A    4/2005

OTHER PUBLICATIONS

Zhang Jin et al., "Insulin disrupts beta-adrenergic signalling to protein kinase A in adipocytes", Nature, Sep. 2005, pp. 569-573, vol. 437, No. 7058, XP002422133 (London).
Baird G S et al. "Circular permutation and receptor insertion within green fluorescent proteins", Proceedings of the National Academy of Sciences of USA, National Academy of Science, Sep. 28, 1999 pp. 11241-11246, vol. 96, No. 20, XP002187230, Biochemistry, (Washington, DC, USA).
Allen Michael D et al. "Subcellular dynamics of protein kinase A activity visualized by FRET-based reporters", Biochemical and Biophysical Research Communications, Sep. 2006, pp. 716-721, vol. 348, No. 2, XP005599167, Elsevier Inc. (USA).
International Search Report of PCT/US2006/041741, completion date Dec. 27, 2007, mail date Mar. 15, 2007.
Written Opinion of of PCT/US2006/041741.

*Primary Examiner* — Anand Desai
*Assistant Examiner* — Samuel Liu
(74) *Attorney, Agent, or Firm* — Banner & Witcoff, Ltd.

(57) ABSTRACT

Protein kinase A reporters useful for obtaining measurements of protein kinase A activity with high spatial and temporal resolution can be used in high throughput assays to identify potentially therapeutic compounds.

19 Claims, 9 Drawing Sheets

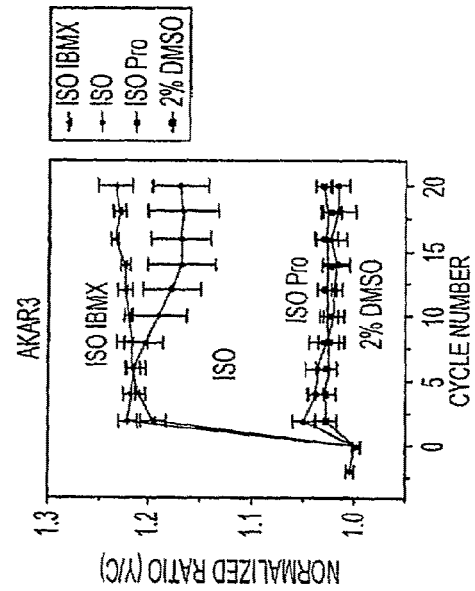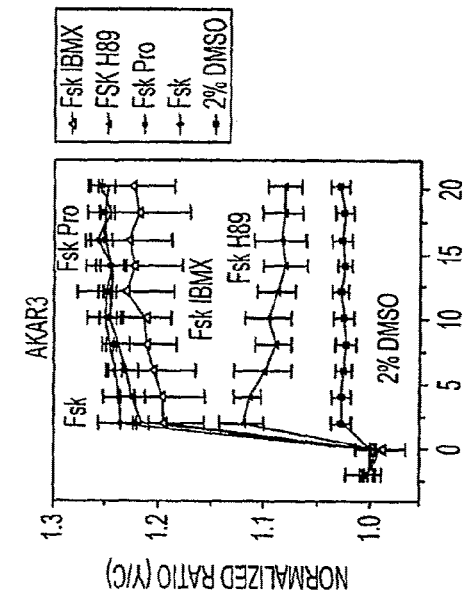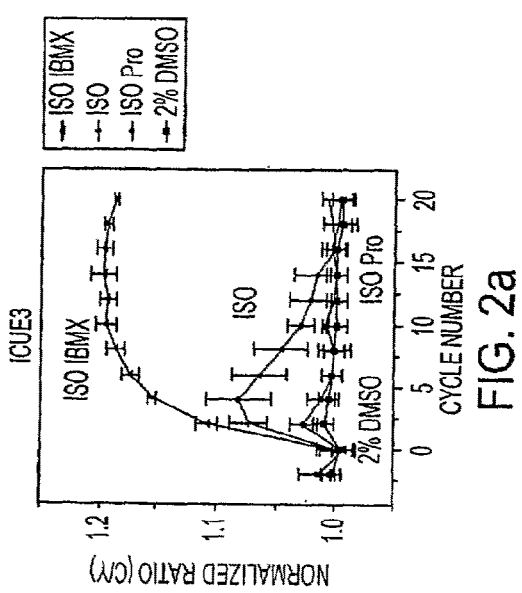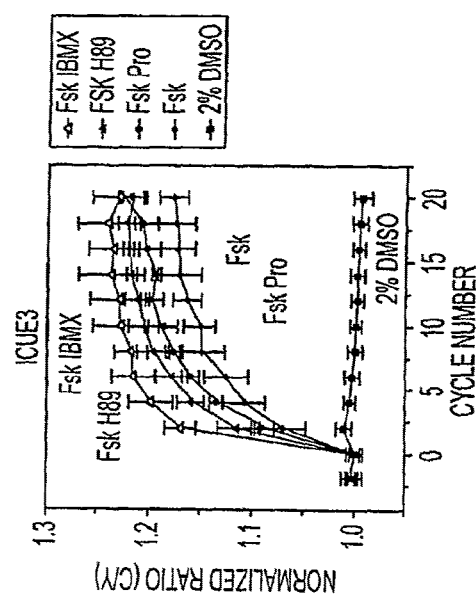
FIG. 2a
FIG. 2b
FIG. 2c
FIG. 2d

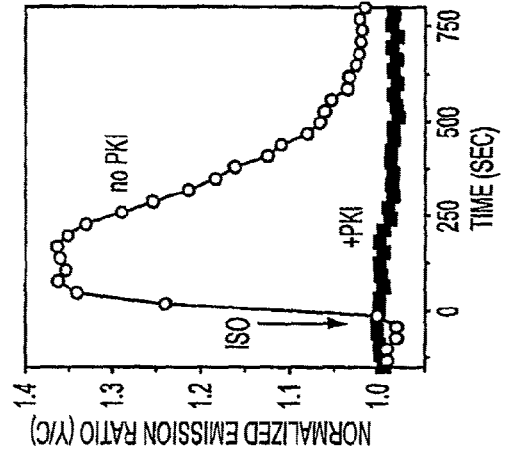
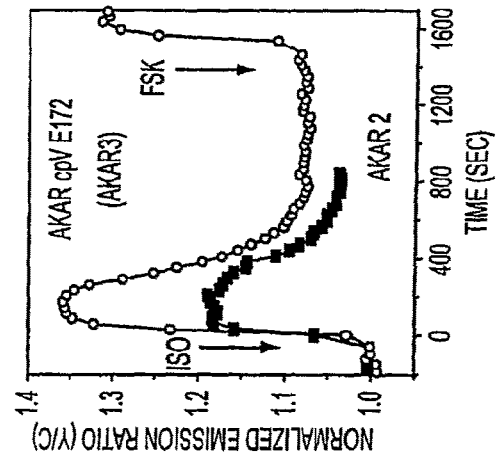
FIG. 4a
FIG. 4b
FIG. 4c

PROTEIN KINASE A REPORTERS USEFUL IN HIGH THROUGHPUT ASSAYS

This application is a national stage application of PCT/US06/41741 filed Oct. 26, 2006, which claims the benefit of Ser. No. 60/730,750 filed Oct. 27, 2005 and 60/800,451 filed May 15, 2006. Each of these applications is incorporated herein by reference in its entirety.

This invention was made using funds from NIH grants CA009243 and DK073368. The government retains certain rights in the invention.

This application incorporates by reference the contents of a 36.8 kb text file labeled "12091858sequencelisting.txt," created on Jul. 11, 2011 which is the sequence listing for this application.

FIELD OF THE INVENTION

The invention relates to detection of protein kinase A (PKA) activity, in particular to use of live cell high-throughput assays based on PKA reporters for drug screens, pharmacological profiling, and functional genomics studies.

BACKGROUND OF THE INVENTION

Genetically-encoded reporters based on fluorescence resonance energy transfer (FRET) have become powerful tools for monitoring the activities of protein kinases and second messengers in live-cell imaging, but their application in high throughput assays has yet to be realized. There is a need in the art for sensitive PKA reporters which can be used for accurate measurements of spatial and temporal PKA activities in living cells.

BRIEF DESCRIPTION OF THE FIGURES

FIG. 1. High-throughput activity assay based on improved A-Kinase Activity Reporter (AKAR).

FIG. 2. High-throughput activity assays for cAMP and PKA in pharmacological profiling. FIGS. 2A and 2C, representative data from five independent runs showing emission ratio (cyan/yellow) changes of ICUE3 in HEK-293 cells treated with indicated drugs. 1 cycle=92 sec. FIGS. 2B and 2D, representative data from five independent runs showing emission ratio (cyan/yellow) changes of AKAR3 in HEK-293 cells treated with indicated drugs. 1 cycle=64 sec. Error bars represent standard deviation (n=3).

FIG. 3. High-throughput screening.

FIG. 4. Improved AKAR. FIG. 4A, domain structure of AKAR constructs with responses (average±standard deviation); AKAR3 contains a circularly permutated Venus (cp Venus E172) as the FRET acceptor. FIG. 4B, representative time course of HEK-293 cells expressing AKAR3 (circles) treated with ISO followed by Fsk stimulation, in comparison to AKAR2 response (squares). An AKAR3 mutant in which the phosphorylation site threonine is mutated to an alanine showed no response. FIG. 4C, treatment of AKAR3-expressing HEK-293 cells with 1 μM ISO in the presence or absence of PKI, a specific peptide inhibitor of PKA.

FIG. 5. Improved ICUE.

DETAILED DESCRIPTION OF THE INVENTION

Figure 1A:
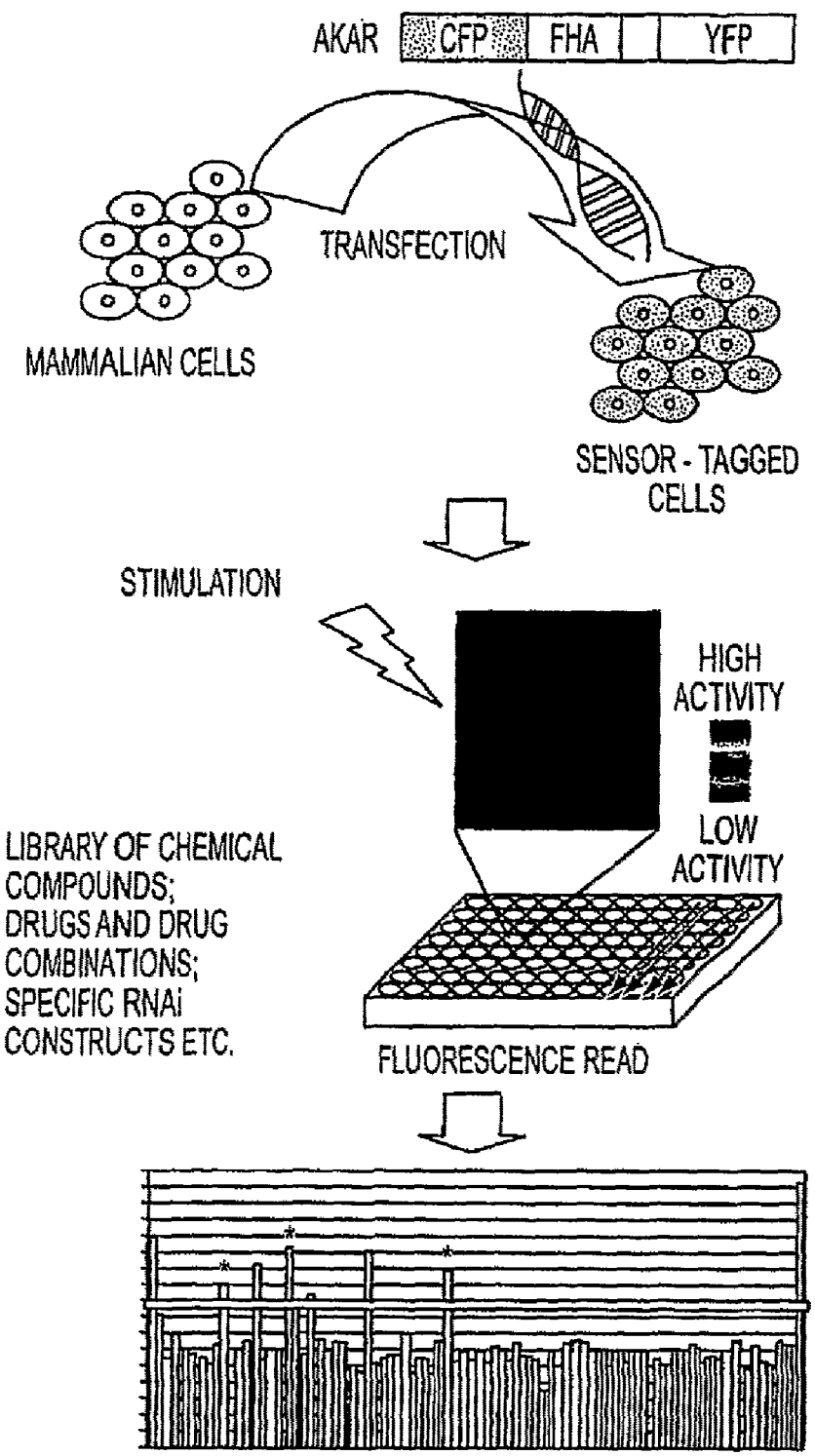
FIG. 1A, scheme for using live cell high-throughput assays based on FRET reporters (e.g., AKAR for PKA activity) for drug screens, pharmacological profiling, and functional genomics studies. In the schematic representation of AKAR, the box between "FHA" and "YFP" is the PKA substrate.

The invention provides highly sensitive reporter molecules by which temporal and spatial protein kinase A (PKA) activity can be determined in living tissues and cells. The invention also provides high-throughput assays that use PKA reporters of the invention. High-throughput assays of the invention permit detection of PKA activity in single, live cells and can be used, inter alia, to screen compounds for their ability to modulate dynamic kinase activities in living cells.

PKA Reporters

PKA reporters of the invention are fusion proteins which comprise a FRET donor and acceptor pair (i.e., a "donor moiety" and "acceptor moiety"; see below) separated by a phosphoamino acid binding domain and a PKA substrate. PKA substrates can be, e.g., LRRATLVD (amino acids 15-22 of SEQ ID NO:3), LRRASLP (SEQ ID NO:20), LRRATLP (SEQ ID NO:21), LRRASP (SEQ ID NO:22), LRRATP (SEQ ID NO:23), RRASFVF (SEQ ID NO:24), RRATFVF (SEQ ID NO:25),), RRXS (SEQ ID NO:26; in which X can be any amino acid), or RRXT (SEQ ID NO:27; (in which X can be any amino acid). Phosphoamino acid binding domains can be, e.g., 14-3-3, isoforms of FHA domains such as FHA-1 and FHA-2, WW domains, or a Polo-box domain. Portions of the PKA reporters are covalently linked to form the fusion proteins. "Covalently linked" according to the invention includes direct covalent linkage and linkage by way of covalent bonds to an amino acid linker sequence.

In one embodiment, a PKA reporter of the invention ("AKAR3"; SEQ ID NO:1) comprises, from N to C terminus, (a) amino acids 1-227 of enhanced cyan fluorescent protein (ECFP$^{1-227}$) (e.g., amino acids 1-228 of SEQ ID NO:1; (b) a forkhead associated domain 1 (FHA1; e.g., amino acids 232-373 of SEQ ID NO:1) covalently linked to the ECFP$^{1-227}$ with an amino acid linker RMH; (c) the amino acid sequence AGTKPGSGEGSTKGLRRATLVDGGTGGSEL (SEQ ID NO:3) covalently linked to the FHA1; and (d) a circularly permuted variant of yellow fluorescent protein (e.g., amino acids 403-647 of SEQ ID NO:1) covalently linked to the amino acid sequence SEQ ID NO:3. SEQ ID NO:3 comprises a PKA substrate (amino acids 15-22 of SEQ ID NO:3) and two amino acid linkers (amino acids 1-14 and 23-30 of SEQ ID NO:3). AKAR3 has shows an increase in emission ratio (yellow over cyan) of about 40%.

In another embodiment, a PKA reporter ("GRet_AKAR"; SEQ ID NO:18) comprises, from N to C terminus, (a) a green fluorescent protein (e.g., amino acids 1-228 of SEQ ID NO:18); (b) a forkhead associated domain 1 (FHA1) covalently linked to the green fluorescent protein with an amino acid linker RMH; (c) the amino acid sequence SEQ ID NO:3 covalently linked to the FHA1; and (d) a red fluorescent protein (e.g., amino acids 403-638 of SEQ ID NO:18) covalently linked to the amino acid sequence SEQ ID NO:3.

In yet another embodiment, a PKA reporter ("AKAR3.2"; SEQ ID NO:4) comprises, from N to C terminus, (a) a cerulean fluorescent protein (e.g., amino acids 1-239 of SEQ ID NO:4); (b) a forkhead associated domain 1 (FHA1) covalently linked to the cerulean protein with an amino acid linker RMH; (c) the amino acid sequence SEQ ID NO:3 covalently linked to the FHA1; and (d) a circularly permuted variant of yellow fluorescent protein (e.g., amino acids 414-658 of SEQ ID NO:4) covalently linked to the amino acid sequence SEQ ID NO:3. Because of the enhanced brightness of the Cerulean fluorescent protein as compared to eCFP, AKAR3.2 has a dynamic range of 55-65%.

Donor and Acceptor Moieties

As used here, a "donor moiety" is a fluorophore or a luminescent moiety. The absorption spectrum of the "acceptor moiety" overlaps the emission spectrum of the donor moiety. The acceptor moiety does not need to be fluorescent and can be a fluorophore, chromophore, or quencher. In some embodiments both the donor and acceptor moieties are fluorescent proteins. In other embodiments both the donor and acceptor moieties are luminescent moieties. In yet other embodiments, either one of the donor or acceptor moieties can be a fluorescent protein while the other moiety is a luminescent moiety. In other embodiments, the acceptor moiety is a "quencher moiety."

When both the donor and acceptor moieties are fluorophores, resonance energy transfer is detected as "fluorescence resonance energy transfer" (FRET). If a luminescent moiety is involved, resonance energy transfer is detected as "luminescent resonance energy transfer" (LRET). LRET includes "bioluminescent resonance energy transfer" (BRET; Boute et al., *Trends Pharmacol. Sci.* 23, 351-54, 2002; Ayoub et al., *J. Biol. Chem.* 277, 21522-28, 2002). Because excitation of the donor moiety does not require exogenous illumination in an LRET method, such methods are particularly useful in live tissue and animal imaging, because penetration of the excitation light is no longer a concern. LRET methods have a high contrast and high signal-to-noise ratio; 2) no photobleaching occurs; and 3) quantification is simplified because the acceptor moiety is not directly excited.

Suitable acceptor moieties include, for example, a coumarin, a xanthene, a fluorescein, a fluorescent protein, a circularly permuted fluorescent protein, a rhodol, a rhodamine, a resorufin, a cyanine, a difluoroboradiazaindacene, a phtalocyanine, an indigo, a benzoquinone, an anthraquinone, an azo compound, a nitro compound, an indoaniline, a diphenylmethane, a triphenylmethane, and a zwifterionic azopyridinium compound.

Suitable donor moieties include, but are not limited to, a coumarin, a xanthene, a rhodol, a rhodamine, a resorufin, a cyanine dye, a bimane, an acridine, an isoindole, a dansyl dye, an aminophthalic hydrazide, an aminophthalimide, an aminaphthalimide, an aminobenzofuran, an aminoquinoline, a dicyanohydroquinone, a semiconductor fluorescent nanocrystal, a fluorescent protein, a circularly permuted fluorescent protein, and fluorescent lanthanide chelate.

Fluorescent Proteins

In some preferred embodiments either or both of the donor and acceptor moieties is a fluorescent protein. Suitable fluorescent proteins include green fluorescent proteins (GFP), red fluorescent proteins (RFP), yellow fluorescent proteins (YFP), and cyan fluorescent proteins (CFP). Useful fluorescent proteins also include mutants and spectral variants of these proteins which retain the ability to fluoresce.

RFPs include *Discosoma* RFPs, such *Discosoma* DsRed (SEQ ID NO:6) or a mutant thereof which includes an Ile125Arg mutation, or a non-oligomerizing tandem DsRed containing, for example, two RFP monomers linked by a peptide linker. For example, a non-oligomerizing tandem RFP can contain two DsRed monomers or two mutant DsRed-I125R monomers linked by a peptide (having, for example, the amino acid sequence shown in SEQ ID NO:7).

Useful GFPs include an *Aequorea* GFP (e.g., SEQ ID NO:8), a *Renilla* GFP, a *Phialidium* GFP, and related fluorescent proteins for example, a cyan fluorescent protein (CFP), a yellow fluorescent protein (YFP), or a spectral variant of the CFP or YFP. CFP (cyan) and YFP (yellow) are color variants of GFP. CFP and YFP contain 6 and 4 mutations, respectively. They are Tyr66Try, Phe66Leu, Ser65Thr, Asn145Ile, Met153Thr, and Val163Ala in CFP and Ser65Gly, Val168Leu, Ser72Ala, and Thr203Tyr. Spectral variants include an enhanced GFP (EGFP; SEQ ID NO:9), an enhanced CFP (ECFP; SEQ ID NO:10), an enhanced YFP (EYFP; SEQ ID NO:11), and an EYFP with V68L and Q69K mutations. Other examples of fluorescent proteins comprising mutations are Aequorea GFP with one or more mutations at amino acid residues A206, L221 or F223 of SEQ ID NO:8 (e.g., mutations A206K, L221K, F223R, Q80R); mutations L221K and F223R of ECFP (SEQ ID NO:9), and EYFP V68L/Q69K of SEQ ID NO:8. See also US 2004/0180378; U.S. Pat. Nos. 6,150,176; 6,124,128; 6,077,707; 6,066,476; 5,998,204; and 5,777,079; Chalfie et al., *Science* 263:802-805, 1994.

Other useful GFP-related fluorescent proteins include those having one or more folding mutations, and fragments of the proteins that are fluorescent, for example, an *A. victoria* GFP from which the two N-terminal amino acid residues have been removed. Several of these fluorescent proteins contain different aromatic amino acids within the central chromophore and fluoresce at a distinctly shorter wavelength than the wild type GFP species. For example, the engineered GFP proteins designated P4 and P4-3 contain, in addition to other mutations, the substitution Y66H; and the engineered GFP proteins designated W2 and W7 contain, in addition to other mutations, Y66W.

Folding mutations in *Aequorea* GFP-related fluorescent proteins improve the ability of the fluorescent proteins to fold at higher temperatures and to be more fluorescent when expressed in mammalian cells, but have little or no effect on the peak wavelengths of excitation and emission. If desired, these mutations can be combined with additional mutations that influence the spectral properties of GFP to produce proteins with altered spectral and folding properties, and, particularly, with mutations that reduce or eliminate the propensity of the fluorescent proteins to oligomerize. Folding mutations, with respect to SEQ ID NO:8, include the substitutions F64L, V68L, S72A, T44A, F99S, Y145F, N146I, M153T, M153A, V163A, I167T, S175G, S205T, and N212K.

Luminescent Moieties

Luminescent moieties useful in a cAMP reporter include lanthanides, which can be in the form of a chelate, including a lanthanide complex containing the chelate (e.g, β-diketone chelates of cerium, praseodymium, neodymium, promethium, samarium, europium, gadolinium, terbium, dysprosium, holmium, erbium, thulium, or ytterbium). Lanthanide chelates are well known in the art. See Soini and Kojola, *Clin. Chem.* 29, 65, 1983; Hemmila et al., *Anal. Biochem.* 137, 335 1984; Lovgren et al., In: Collins & Hoh, eds., *Alternative Immunoassays*, Wiley, Chichester, U.K., p. 203, 1985; Hemmila, *Scand. J. Clin. Lab. Invest.* 48, 389, 1988; Mikola et al., *Bioconjugate Chem.* 6, 235, 1995; Peruski et al., *J. Immunol. Methods* 263, 35-41, 2002; U.S. Pat. Nos. 4,374,120; and 6,037,185. Suitable β-diketones are, for example, 2-naphthoyltrifluoroacetone (2-NTA), 1-naphthoyltrifluoroacetone (1-NTA), p-methoxybenzoyltrifluoroacetone (MO-BTA), p-fluorobenzoyltrifluoroacetone (F-BTA), benzoyltrifluoroacetone (BTA), furoyltrifluoroacetone (FTA), naphthoylfuroylmethane (NFM), dithenoylmethane (DTM), and dibenzoylmethane (DBM). See also US 20040146895.

Luminescent proteins include, but are not limited to, lux proteins (e.g., luxCDABE from *Vibrio fischerii*), luciferase proteins (e.g., firefly luciferase, *Gaussia* luciferase, *Pleuromamma* luciferase, and luciferase proteins of other beetles, Dinoflagellates (*Gonylaulax; Pyrocystis*), Annelids (*Dipocardia*), Molluscs (*Lativa*), and Crustacea (*Vargula; Cypridina*), and green fluorescent proteins of bioluminescent coelenterates (e.g., *Aequorea Victoria, Renilla mullerei, Renilla reniformis*; see Prendergast et al., *Biochemistry* 17, 3448-53, 1978; Ward et al., *Photochem. Photobiol.* 27, 389-96, 1978; Ward et al., *J. Biol. Chem.* 254, 781-88, 1979; Ward et al., *Photochem. Photobiol. Rev* 4, 1-57, 1979; Ward et al., *Biochemistry* 21, 4535-40, 1982). Many of these proteins are commercially available. Firefly luciferase is available from Sigma, St. Louis, Mo., and Boehringer Mannheim Biochemicals, Indianapolis, Ind. Recombinantly produced firefly luciferase is available from Promega Corporation, Madison, Wis. Jellyfish aequorin and luciferase from *Renilla* are commercially available from Sealite Sciences, Bogart, Ga.

The DNA sequences of the aequorin and other luciferases employed for preparation of some cAMP reporters of the invention can be derived from a variety of sources. For example, cDNA can be prepared from mRNA isolated from the species disclosed above. See Faust, et al., *Biochem.* 18, 1106-19, 1979; De Wet et al., *Proc. Natl. Acad. Sci. USA* 82, 7870-73, 1985.

Luciferase substrates (luciferins) are well known and include coelenterazine (available from Molecular Probes, Eugene, Oreg.) and ENDUREN™. These cell-permeable reagents can be directly administered to cells, as is known in the art. Luciferin compounds can be prepared according to the methods disclosed by Hori et al., *Biochemistry* 14, 2371-76, 1975; Hori et al., *Proc. Natl. Acad. Sci. USA* 74, 4285-87, 1977).

Dark Quenchers

In some embodiments the acceptor moiety is a quencher moiety, preferably a "dark quencher" (or "black hole quencher") as is known in the art. In this case, the change in conformation which occurs upon cAMP binding eliminates quenching, resulting in an increase in energy emission from the donor moiety. "Dark quenchers" themselves do not emit photons. Use of a "dark quencher" reduces or eliminates background fluorescence or luminescence which would otherwise occur as a result of energy transfer from the donor moiety. Suitable quencher moieties include dabcyl (4-(4'-dimethylaminophenylazo)-benzoic acid), QSY™-7 carboxylic acid, succinimidyl ester (N,N'-dimethyl-N,N'-diphenyl-4-((5-t-butoxycarbonylaminopentyl)aminocarbon yl) piperidinylsulfone-rhodamine (a diarylrhodamine derivative from Molecular Probes, Eugene, Oreg.). Suitable quencher moieties are disclosed, for example, in US 2005/0118619; US 20050112673; and US 20040146959.

Any suitable fluorophore may be used as the donor moiety provided its spectral properties are favorable for use with the chosen dark quencher. The donor moiety can be, for example, a Cy-dye, Texas Red, a Bodipy dye, or an Alexa dye. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, a fluorescein (e.g., fluorescein, tetrachlorofluorescein, hexachlorofluorescein), rhodamine, tetramethylrhodamine, or other like compound. Suitable fluorescent moieties for use with dark quenchers include xanthene dyes, such as fluorescein or rhodamine dyes, including 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS).

Other suitable fluorescent moieties include coumarins, such as 3-phenyl-7-isocyanatocoumarin; acridines, such as 9-isothiocyanatoacridin-e and acridine orange; N-(p-(2-benzoxazolyl)phenyl)maleimide; cyanines, such as indodicarbocyanine 3 (Cy3), indodicarbocyanine 5 (Cy5), indodicarbocyanine 5.5 (Cy5.5), 3-1-carboxy-pentyl)-3'-ethyl-5,5'-dimethyl-loxacarbocyanine (CyA); 1H,5H,1H,15H-Xantheno[2,3,4-ij:5,6,7-i'j']diquinol-izin-18-ium, 9-[2(or 4)-[[[6-[2,5-dioxo-1-pyrrolidinyl)oxy]-6-oxohexyl]amino]sulfonyl]-4(or 2)-sulfophenyl]-2,3,6,7,12,13,16,17-octahydro-inner salt (TR or Texas Red); BODIPY™ dyes; benzoxaazoles; stilbenes; pyrenes; and the like.

Subcellular Targeting Sequences

PKA reporters of the invention optionally can include a subcellular targeting sequence which can target a PKA reporter to a subcellular domain such as a plasma membrane, a nuclear membrane, a cytosol, an endoplasmic reticulum, a mitochondria, a mitochondrial matrix, a chloroplast, a medial trans-Golgi cistemae, a lumen of a lysosome, or a lumen of an endosome. Many such targeting sequences are known in the art. Examples include the plasma membrane targeting sequence shown in SEQ ID NO:12, the nuclear localization signal sequence shown in SEQ ID NO:13, the mitochondrial localization sequence shown in SEQ ID NO:14, and the mitochondrial matrix targeting signal shown in SEQ ID NO:15. Targeting sequences can be linked to PKA reporters using, for example, a tetracysteine motif such as Cys Cys Xaa Xaa Cys Cys (SEQ ID NO:16). Targeting sequences can be linked at either the N- or C-terminus of a PKA reporter or at intermediate points in the reporter.

Assembly of PKA Reporters

PKA reporters of the invention are fusion proteins and preferably are expressed recombinantly. The invention provides nucleic acid molecules for this purpose. A nucleic acid molecule encoding a PKA reporter can comprise any nucleotide sequence which encodes the amino acid sequence of the reporter. Particular nucleic acid sequences are provided as SEQ ID NO:2 (AKAR3), SEQ ID NO:5 (AKAR3.2), and SEQ ID NO:18 (GRet_AKAR). Nucleic acid molecules of the invention include single- and double-stranded DNA (including cDNA) and mRNA. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

In some embodiments the nucleic acid molecules are expression constructs which contain the necessary elements for the transcription and translation of an inserted coding sequence encoding a PKA reporter. Expression constructs can be used as vectors for introducing PKA reporters into cells. Methods which are well known to those skilled in the art can be used to construct expression vectors containing sequences encoding PKA reporters and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

Expression vectors of the invention can be expressed in a variety of host cells. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems, particularly mammalian systems, including human systems. See WO 01/98340, which is incorporated herein by reference in its entirety. The choice of vector components and appropriate host cells is well within the capabilities of those skilled in the art.

Alternatively, protein or non-protein donor and/or acceptor moieties can be linked to the polypeptide by covalent attachment. There are a variety of methods known in the art which are useful for this purpose. For example, the attachment can be direct, via a functional group on the polypeptide (e.g., amino, carboxyl and sulfhydryl groups) and a reactive group on the fluorophore. Free amino groups in the polypeptide can be reacted with fluorophores derivatized with isothiocyanate, maleic anhydride, N-hydroxysuccinimide, tetrafluorylphenyl and pentafluoryl esters. Free carboxyl groups in the polypeptide can be reacted with carbodiimides such as 1-ethyl-3-[dimethylaminopropyl]carbodiimide hydrochloride to create a reactive moiety that will react with an amine moiety on the donor or acceptor moiety. Sulfhydryl groups can be attached to donor or acceptor moieties modified with maleimide and iodoacetyl groups, although such linkages are more susceptible to reduction than linkages involving free amino groups. The polypeptide can also be linked indirectly via an intermediate linker or spacer group, using chemical groups such as those listed above.

It is also possible to produce PKA reporters of the invention using chemical methods to synthesize the amino acid sequence of the polypeptide and, optionally, one or more fluorescent or luminescent proteins. Methods include direct peptide synthesis using solid-phase techniques (Merrifield, *J. Am. Chem. Soc.* 85, 2149-2154, 1963; Roberge et al., *Science* 269, 202-204, 1995). Protein synthesis can be performed using manual techniques or by automation. Automated synthesis can be achieved, for example, using Applied Biosystems 431A Peptide Synthesizer (Perkin Elmer). Optionally, fragments of polypeptide portions of PKA reporters can be separately synthesized and combined using chemical methods to produce a full-length reporter molecule. See WO 01/98340.

Delivery of PKA Reporters to Cells

PKA reporters of the invention can be introduced into cells in vitro using reversible permeabilization techniques. See U.S. Pat. Nos. 6,127,177; 6,902,931; Russo et al., *Nature Biotechnology* 15, 278-82, Mar. 1997; Santangelo et al., *Nucleic Acids Res.* 32, 1-9, Apr. 14, 2004.

Expression vectors comprising a PKA reporter-encoding nucleotide sequence can be transfected into any cell in vitro in which it is desired to monitor PKA activity. Any transfection method known in the art can be used, including, for example, including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Useful vectors and methods of delivering the vectors to cells in vivo are disclosed, for example, in U.S. Pat. Nos. 6,825,012; 6,878,549; 6,645,942 6,692,737; 6,689,758; 6,669,935; and 6,821,957.

Methods of Detecting PKA Activity

The invention provides various methods for detecting PKA activity by detecting conformational changes in a PKA reporter. Broadly, the methods involve detecting a change in resonance energy transfer of a PKA reporter of the invention when the reporter is subjected to an increase or decrease in PKA activity. PKA acts on the PKA substrate portion of the PKA reporter to induce a conformational change that changes resonance energy transfer from the donor moiety to the acceptor moiety.

A change in resonance energy transfer can readily be detected using methods well known in the art. See, e.g., US 2005/0118619; US 2002/0137115; US 2003/0165920; US 2003/0186229; US 2004/0137479; US 2005/0026234; US 2005/0054573; US 2005/0118619; U.S. Pat. Nos. 6,773,885; 6,803,201; 6,818,420; Ayoub et al., 2002; Boute et al., 2002; Domin et al., *Prog. Biomed. Optics and Imaging, Proc. SPIE*, vol 5139, 2003, pp 238-242; Evellin et al., *Methods Mol. biol.* 284, 259-70, 2004; Honda et al., *Proc. Natl. Acad. Sci. USA* 98, 437-42, Feb. 27, 2001; Honda et al., *Methods Mol. Biol.* 3, 27-44, 1005; Mongillo et al., *Cir. Res.* 95, 67-75, Jul. 9, 2004; Mongillo et al., *Methods Mol. Biol.* 307, 1-14, 2005; Nagai et al., *Proc. Natl. Acad. Sci. USA* 101, 10554-59, Jul. 20, 2004; Nikolaev et al., *J. Biol. Chem.* 279, 37215-18, 2004; Polit et al., *Eur. J. Biochem.* 270, 1413-23, 2003; Ponsioen et al., *EMBO Rep.* 5, 1176-80, 2004; Santangelo et al., *Nucl. Acids Res.* 32, 1-9, e-published Apr. 14, 2004; and Warrier et al., *Am. J. Physiol. Cell Phiol.* 289, C455-61, August 2005. Properties which can be detected as resonance energy transfer (RET) measurements include a quantum efficiency, an excitation spectrum, an emission spectrum, an excitation wavelength maximum, an emission wavelength maximum, a ratio of excitation amplitudes at two wavelengths, a ratio of emission amplitudes at two wavelengths, an excited state lifetime, anisotropy, a polarization of emitted light, resonance energy transfer, and a quenching of emission at a wavelength.

PKA reporters of the invention can be used in cell-free systems, in isolated cells (for example, in primary cell culture or a cell line) or in cells in situ (e.g., in an isolated tissue sample, an isolated whole organ, or in a mammal). Subcellular distribution of PKA activity or changes in PKA activity can be detected, for example, as described in the specific Examples, below. Absolute PKA activity levels can be detected by obtaining a RET measurement in the assay system and comparing it to a standard curve obtained in vitro.

Simultaneous or Parallel Monitoring of Camp Dynamics and PKA Phosphorylation

Soluble adenylyl cyclase and regulatory and catalytic subunits of PKA coexist in the nucleus of mammalian cells (Zippin et al., *J. Cell Biol.* 164, 527-34, 2004). Assays can be carried out using PKA reporters of the invention together with targeted cAMP indicators to examine the temporal correlation of cAMP dynamics and PKA activation within single living cells. For example, a plasma membrane-targeted cAMP reporter and a nuclear-localized PKA reporter can be co-expressed in cells such as HEK-293 cells (see WO 2006/023972). If desired, the assays can be carried out in a high-throughput format (see below). Useful cAMP reporters are disclosed in WO 2006/023972.

cAMP dynamics and PKA phosphorylation can be monitored either simultaneously or in parallel. Simultaneous assays can be carried out using targeted versions of the reporters. Parallel assays can be carried out using reporters comprising different colors of fluorescent protein.

In some embodiments, steady-state RET measurements are first obtained and then measurements are taken after addition of a test compound to the assay system. The effects of the test compounds on cAMP concentration and PKA activity can be simultaneously or parallelly monitored by using ICUE and AKAR or to monitor the effect of the test compound on cAMP concentration (e.g., in drug-screening methods). Test compounds can be pharmacologic agents already known in the art to affect PKA activity or can be compounds previously unknown to have such an activity. Compounds known to affect PKA activity include, for example, isoproterenol, epinephrine, ritodrine, 3-isobutyl-1-methylxanthine (IBMX), and H-89.

Test compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection.

Fluorescence activated cell sorting (FACS) is well-suited for use with high throughput methods of the invention. For example, emission ratios of yellow-to-cyan (cyan excitation) for individual cells are detected during the first sorting—not all cells will have the same emission ratio and a distribution for the whole population can be plotted; the cells can be stimulated to activate PKA in the absence or presence of other drugs; emission ratios of individual cells are detected again during the second sorting; the difference in emission ratios, usually presented as a shift in the distribution, will reflect the changes in PKA activity.

High-Throughput Assays

High throughput assays of the invention are generally applicable to all kinase targets within the kinome (see FIG. 1A) and are ideally suited for examining dynamic responses of endogenous kinase targets, for evaluating drug candidates which ultimately perform within cellular environments, and for identifying compounds with unique mechanisms of action. Methods of the invention can be extended to follow multiple components of kinase-mediated signaling pathways to screen for pathway modulators.

High throughput assays of the invention, when combined with use of kinase activity reporters, permit simple, fast, and convenient high-throughput reading of dynamic kinase activities with high spatiotemporal resolution. These methods complement, yet offer unique advantages over, existing methods, including purified target-based biochemical screens and end-point focused phenotypic screens. Activity-based screens of the invention can be combined with phenotypic screens (e.g., Clemons, *Curr. Op. Chem. Biol.* 8, 334-38, 2004) to provide direct measurement of dynamic cellular activities of defined targets or the activity of a signaling pathway. Compared to in vitro assays, living cells are used as reaction vessels with targets of interest, cofactors, and regulators present at endogenous levels in their natural cellular environment, where spatiotemporal control of signaling activities can be specifically followed. With the complexity of live systems maintained, the quality of the screening process is increased, enabling discovery of compounds with unique mechanisms of action. Thus, the simple yet powerful high-throughput activity assays of the invention should find immediate application in high-throughput screens for pharmacological reagents and drug candidates, as well as in parallel tracking of multiple physiological and pharmacological events at subcellular locations in living cells in chemical and functional genomics studies. Furthermore, this assay platform is generally applicable to most kinases in the kinome, as various kinase activity sensors can be engineered and adapted to this assay format.

Kits

The invention provides kits comprising one or more PKA reporters of the invention and, optionally, one or more cAMP reporters. The kits also may provide all or a subset of the reagents that are required for practicing the invention. The kits may comprise written instructions, in paper or electronic form, or a reference to an on-line set of instructions. The instructions may contain data against which the results determined using the kit can be compared. Containers which hold the components of any given kit can vary. The kits may be divided into compartments or contain separate vessels for each component. The components may be mixed together or may be separated. Optional components of the kit include means for collecting, processing, and/or storing test samples.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Methods for Examples 2-7

Gene Construction. Different variants of fluorescent protein were amplified using PCR and incorporated into AKAR2 and AKAR2T391A to replace the original ECFP or citrine (Zhang et al., *Nature* 437, 569-73, 2005). Cytoplasmic targeting of AKAR3 was achieved by genetically adding a nuclear export signal (NES) LPPLERLTL (SEQ ID NO:17) at the C-terminal (Sato et al., *Nat. Biotechnol.* 20, 287-94, 2002). ICUE ("indicator of cAMP using Epac") constructs containing new fluorescent protein variants were created using the same method as above. All constructs were initially generated in pRSET B (Invitrogen), then subcloned to pcDNA3 (Invitrogen) behind a Kozak sequence for mammalian expression save for AKAR3NES, which used 3' restriction sites in pcDNA3 to introduce the NES.

Cell Culture and Imaging. HEK-293 cells were plated onto sterilized glass coverslips in 35 mm dishes and grown to ~50% confluency in DMEM (10% FBS at 37° C. with 5% $CO_2$). Cells were transfected with calcium phosphate and grown for 12-24 hours before imaging. After washing once with Hanks' balanced salt solution (HBSS), cells were maintained in buffer in the dark at 20-25° C. Isoproterenol (ISO; Sigma), forskolin (Fsk; Calbiochem), H89 (Sigma) were added as indicated. Cells were imaged on a Zeiss Axiovert 200M microscope with a 40×/1.3NA oil-immersion objective lens and cooled CCD camera as described in (21). Briefly, dual emission ratio imaging used a 420DF20 excitation filter, a 450DRLP dichroic mirror, and two emission filters (475DF40 for cyan and 535DF25 for yellow). The ratios of yellow-to-cyan (for AKAR) or cyan-to-yellow (for ICUE) emissions were then calculated at different time points and normalized by dividing all ratios by the emission ratio before stimulation, setting basal emission ratio as 1.

Live Cell Plate Reading. HEK-293 cells were transfected with AKAR3 or ICUE3 using calcium phosphate at 40% confluency and grown for 40 hours. Cells were then trypsinized and plated in a Costar 3603 96-well plate (Corning) at a density of 150,000 cells per well. After incubation for another 24 hours, cells were washed once with HBSS and left in 150 µl of HBSS at 20-25° C. Fluorescence reading was taken on a FLUOstar OPTIMA fluorescence microplate reader (BMG Labtechnologies Inc.) using a 420DF20 excitation filter and two emission filters (470DF40 for cyan and 535DF25 for yellow). A baseline was established in three cycles, each consisting of a full plate reading of yellow intensity, followed by a reading of cyan intensity.

Each cycle lasted between 64 and 92 seconds. Cells were then treated with ISO, Fsk, H89, Propranolol (Pro; Sigma), or 3-isobutyl-1-methylxanthine (IBMX; Sigma) as indicated. Readings were taken in additional cycles. FRET change was calculated as the percent increase of emission ratios (yellow-to-cyan for AKAR and cyan-to-yellow for ICUE) over baseline for each well during a given cycle. Several parameters were calculated to assess the efficiency of the assay, including Z' factor, coefficient of variation, and signal to noise (S/N) ratio (22).

Live Cell High-Throughput Screening. HEK-293 cells transiently expressing AKAR or stably expressing ICUE were trypsinized and plated in a Costar 3606 96-well plate (Corning) at a density of 150,000 cells per well. After incubation for 24 hours, cells were washed once with HBSS and left in 190 µl of HBSS at 20-25° C. Fluorescence readings were taken as described above, with each cycle lasting 90 seconds. Following baseline acquisition, cells in each experimental well were treated with a compound from the Johns Hopkins Clinical Compound Library to a final concentration of 10 µM. Control cells were treated with 10 µL of 10% fetal bovine serum (FBS) in a solution of phosphate buffered saline (PBS) at pH 7.4, which is the solution used to dissolve library compounds.

Readings were taken for 10 cycles spanning a time of approximately 15 minutes, after which cells in experimental wells and positive controls were treated with 0.25 µM ISO (AKAR) or 0.25 µM Iso plus 100 µM IBMX (ICUE), while negative controls received 0.5% DMSO in HBSS. Ten final cycles were then performed.

FRET responses were calculated as described above. Negative control (10% FBS, 0.5% DMSO) and positive control (10% FBS, 0.25 µM ISO) curves were generated. Agonist hits were defined as compounds eliciting responses larger than six times the standard deviation above the baseline. Antagonist hits were defined as compounds which decreased the ISO stimulated response by 50% or by six times the standard deviation.

EXAMPLE 2

AKAR3 in Live-Cell Imaging and In Vitro Analysis

Figure 7A:
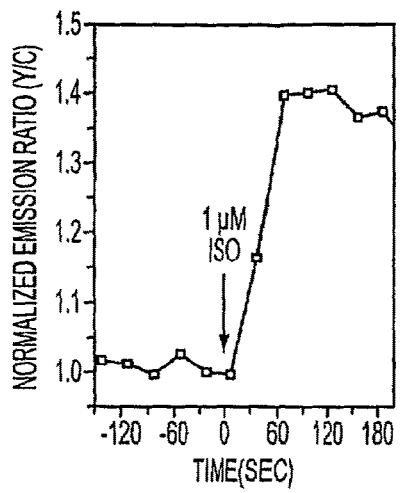
FIG. 7. Further characterization of AKAR3. Representative time courses of plasma membrane-targeted AKAR3 (FIG. 7a) and nuclear-targeted AKAR3 (FIG. 7b) in HEK-293 cells stimulated with 1 μM ISO and 50 μM FSK, respectively.
FIG. 7c, AKAR3-expressing HEK-293 cells were treated with 200 nM phorbol dibutyrate (PDBu), a protein kinase C activator, followed by the addition of 1 μM isoproterenol, then 50 μM forskolin.
FIG. 7d, representative time courses of the emission ratio change of AKAR3 in the presence (closed squares) and absence (open circles) of the specific PKA inhibitor, PKI.
FIG. 7e, emission spectra of the purified AKAR3 before (squares) and after (diamonds) phosphorylation by PKA (excitation 434 nm). The curve using triangle symbols depicts the spectrum of the reporter after digestion with trypsin to quench the energy transfer and quantify the FRET.
FIG. 7*f*, a representative phosphorylation time course for purified AKAR3 protein in the presence of PKA catalytic subunit and 1 mM ATP.
Figure 7B:
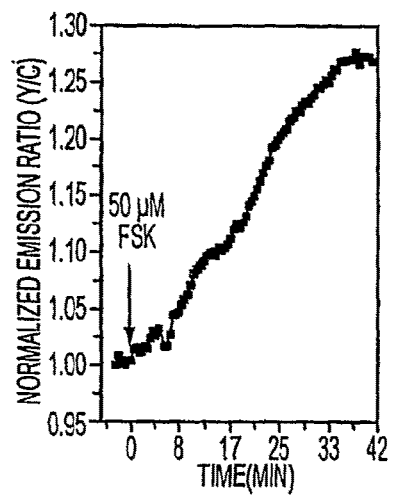

One of the important advantages of genetically encoded reporters of the invention is that they can be targeted to subcellular locations via various targeting motifs. However, in some cases, subcellular targeting may sacrifice the response amplitude of a reporter. To determine whether the improved dynamic range of AKAR3 leads to sensitive detection of subcellular PKA activities, AKAR3 was targeted to two cellular compartments. By attaching a lipid modification domain (Ananthanarayanan et al., *Proc. Natl. Acad. Sci. USA* 2005 Oct 18;102(42):15081-6), the reporter was successfully targeted to the plasma membrane, where it produced an average response of 34.3%±5.4% (n=3) after ISO stimulation (FIG. 7a). Nuclear localization also had minimal effect on the performance of AKAR3 (FIG. 7b). The average nuclear response upon stimulation with FSK was 38.6%±8.45% (n=3) with slower kinetics, consistent with the translocation of the catalytic subunit into the nucleus after cytoplasmic activation. This demonstrates that AKAR3 can be targeted to subcellular compartments while maintaining improved dynamic range.

Figure 7C:
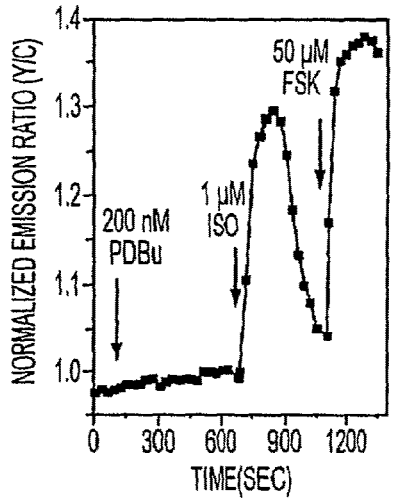
Figure 7D:
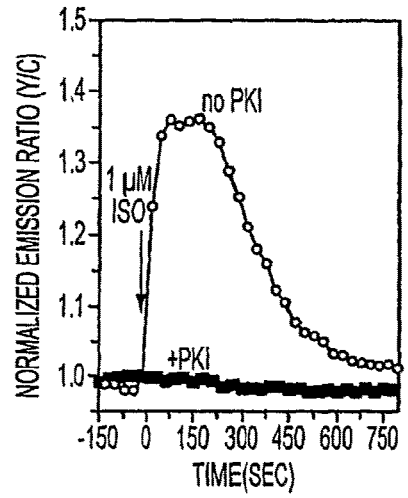

Furthermore, AKAR3 maintained its specificity in sensing active PKA but not protein kinase C (FIG. 7c) or calmodulin-dependent protein kinase II. Co-expression of a PKA catalytic subunit inhibitor, PKI (FIG. 7d), or pretreatment with a PKA inhibitor, H89, both abolished the AKAR3 response, indicating that the response is PKA specific. In addition, when the designated threonine with the AKAR substrate LRRATLVD (amino acids 15-22 of SEQ ID NO:3) was mutated to alanine, responses to ISO and FSK were lost completely, indicating that this residue is the crucial PKA phosphorylation site required for the FRET change.

Figure 7E:
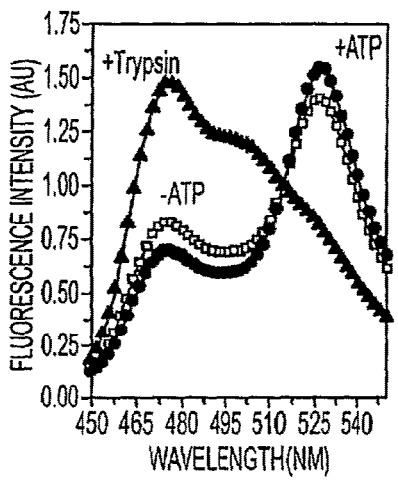
Figure 7F:
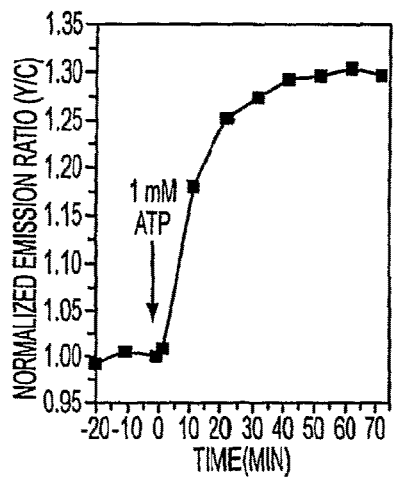

Lastly, in vitro kinase assays were carried out using purified AKAR3 protein from mammalian cell lysates. As shown in FIG. 7e, phosphorylation by catalytic subunit of PKA in the presence of ATP increased the cpVenus emission at 527 nm at the expense of ECFP emission at 475-500 nm, indicating a substantial increase in FRET between the two fluorophores (FIG. 7e). Over a span of approximately 40 minutes after addition of ATP, the emission ratio of AKAR3 increased 29.1%±1.11% (n=2) (FIG. 7f). The FRET efficiencies were quantified using trypsin to separate CFP and cpV without destroying either fluorescent protein and found to be 38.8%±7.36% and 47.2%±7.67% (n=2) before and after phosphorylation, respectively.

EXAMPLE 3

Figure 1B:
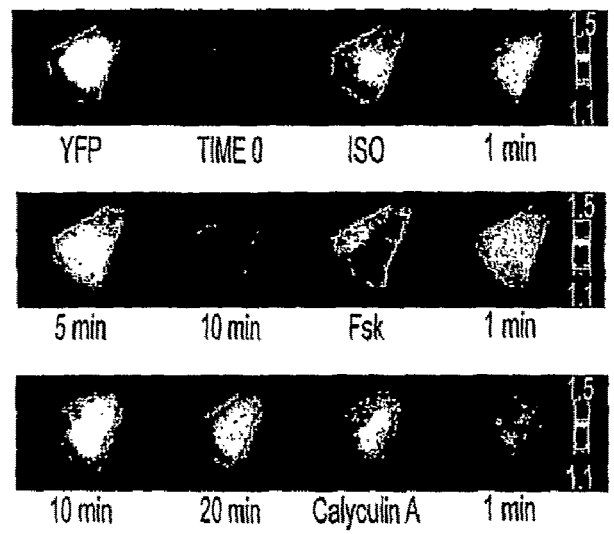
FIG. 1B, representative time course of emission ratio (yellow/cyan) change of AKAR3, indicated by pseudocolor images. A HEK-293 cell expressing AKAR3 was stimulated with 1 μM isoproterenol (ISO), followed by 50 μM forskolin (Fsk), or calyculin A (a phosphatase inhibitor).
Figure 1C:
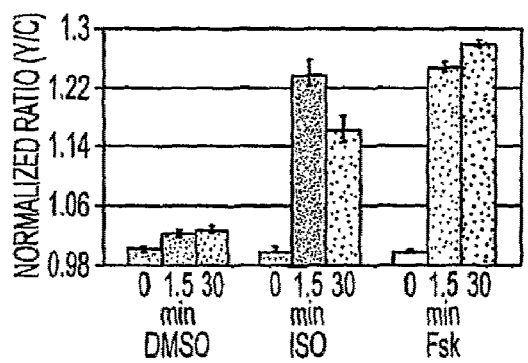
FIG. 1C, representative data from five independent runs in 96-well format showing emission ratio (yellow/cyan) changes of AKAR3 in HEK-293 cells treated with ISO, Fsk, or 2% dimethylsulfoxide (DMSO).

Ratiometric Readout of A-Kinase Activity Reporter (AKAR) in a High-Throughput Plate Reader Format We generated an improved version of AKAR that doubled the response amplitude of
AKAR2 (FIG. 4). This reporter, AKAR3 (FIG. 1b), was tested in a 96-well plate format. Addition of β-adrenergic agonist isoproterenol (ISO) to HEK-203 cells expressing AKAR3 in 06well plates induced an increase in yellow-to-cyan emission ratio of 22.1%±0.7% (n=3), followed by a slight decrease (FIG. 1c). When cells were treated with adenylyl cyclase activator forskolin (Fsk), sustained responses were observed, as shown in single cell imaging (FIG. 1b), with an average emission ratio change of 25.7%±0.7% (n=3). As negative controls, addition of buffer of 2% DMSO generated minimal changes in emission ratios. This 96-well plate assay was sensitive and reproducible, with a signal to noise ratio of 30.3, a Z' factor of 0.84, and a coefficient of variation (CV) of 1.8% for the Fsk-stimulated response.

EXAMPLE 4

Specific Readout of Compartmentalized PKA Activities

Figure 1D:
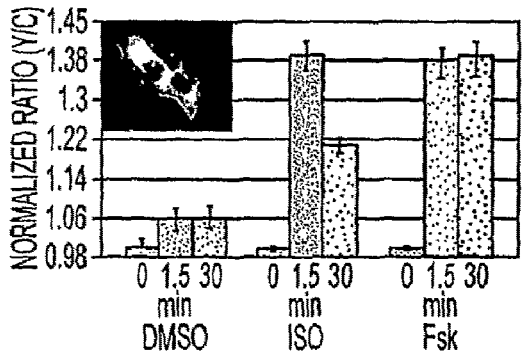
FIG. 1D, representative data from three independent runs showing emission ratio (yellow/cyan) changes of AKAR3 NES (nuclear export signal) in HEK-293 cells treated with indicated drugs. The inset shows a representative fluorescence image of cells expressing AKAR NES. Error bars represent standard deviation (n=3).

Kinase activities are often spatially compartmentalized, and compounds targeting spatiotemporal regulation of kinases could be new classes of modulators. To provide specific readout of compartmentalized PKA activities, we introduced a C-terminal nuclear export signal (NES) to AKAR3. In the plate reader assay using AKAR3-NES (FIG. 1d), cytosolic PKA activity was recorded without contamination of nuclear activity, which has slower kinetics due to diffusional translocation of the catalytic subunit from cytosol to nucleus. As a result, ISO stimulated a larger increase in emission ratio followed by a more rapid decrease than that in the AKAR3 assay (FIG. 1d). The maximum signal for the assay also improved, showing a ratio change of 37.8% ±3.2% (n=3). Thus, sensor targeting provides increased temporal and spatial resolution and can be used to reveal how individual signaling microdomains, such as kinase-containing signaling complexes, are affected by drugs or other perturbations, adding another level of capacity to the non-image-based high-throughput assays of the invention.

EXAMPLE 5

Live Cell High-Throughput cAMP Assay

This example demonstrates a live cell high-throughput cAMP assay, developed as a functional assay for Gs-coupled GPCRs, which demonstrates that both the assay platform and sensor improvement strategy is generally applicable.

Figures 5A, 5B:
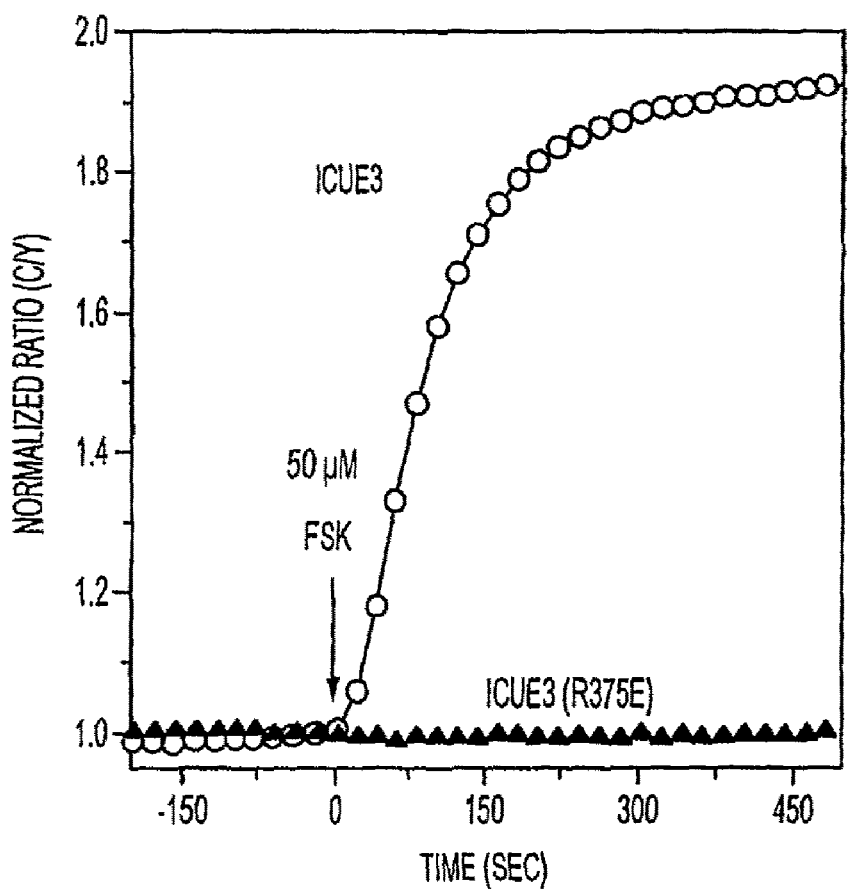
FIG. 5A, domain structure of ICUE3, which contains a circularly permutated Venus (cp Venus L194) as the FRET acceptor.
FIG. 5B, representative time courses of HEK-293 cells expressing ICUE3 (circles) and ICUE3 (R375E) (triangles), treated with 50 μM Fsk. ICUE3 maintained the specificity for cAMP as a loss-of-function mutation in the cAMP binding site (R375E) abolished the FRET response.
Figure 6:
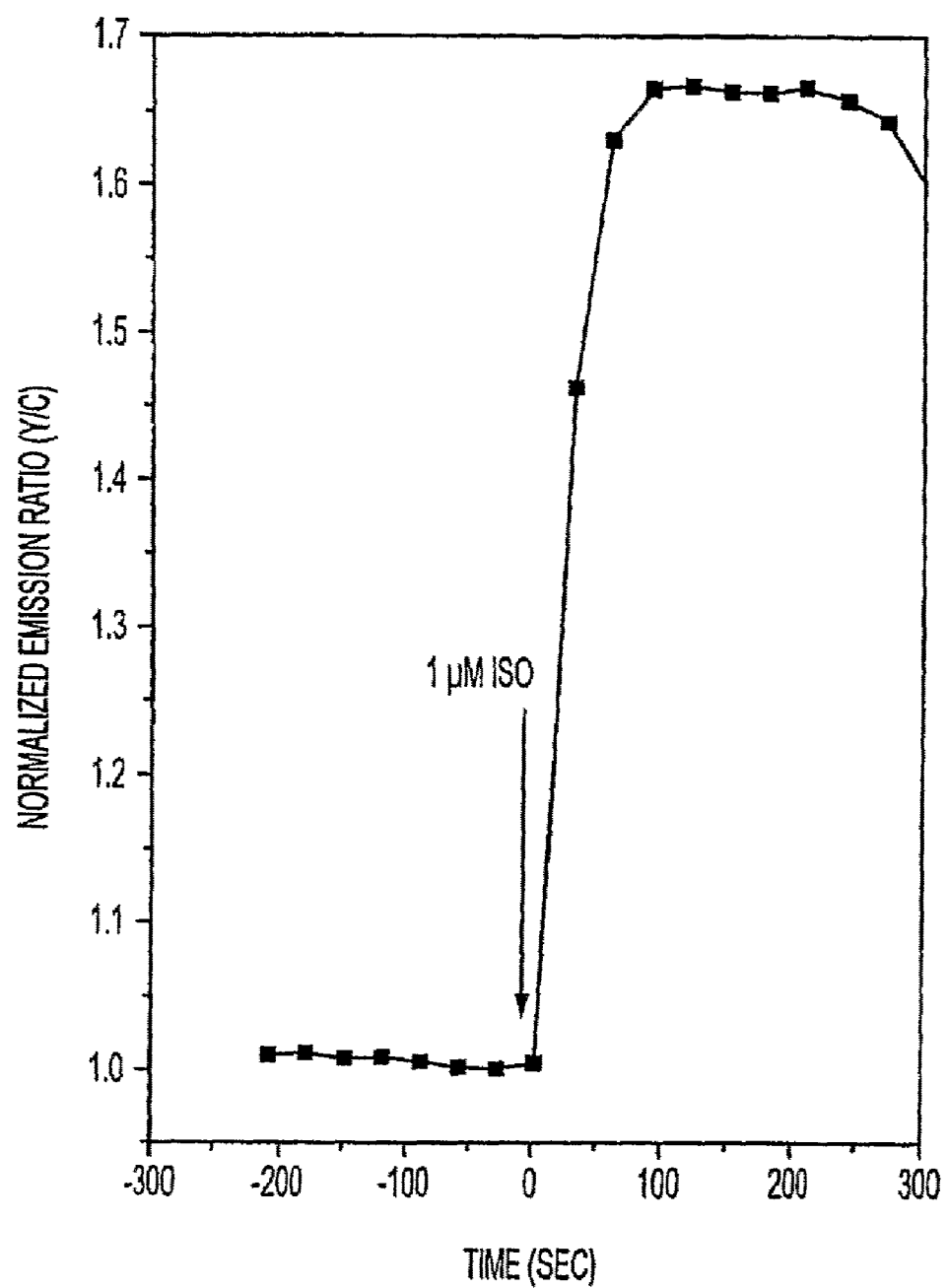
FIG. 6. Representative cellular response using AKAR3.2. HEK-293 cells expressing AKAR3.2 were treated with 1 μM ISO. The subsequent elevation in emission ratio is typical of the new AKAR variant AKAR3.2, showing a maximum response of approximately 65%.

To follow the activity of the signaling pathway and to assay related drug targets in parallel, we developed a live cell-based high-throughput assay for cAMP, a second messenger that is generated via activation of Gs-coupled GPCRs and exerts its effects by activating PKA and other effectors. Similar improvement approaches were first applied to create a reporter that more than doubled the response of previous "Indicator for cAMP Using Epac" (ICUE), which generates a decrease in FRET upon binding of cAMP (FIG. 5). When tested in plate reader format, this improved version ICUE3 showed consistent responses to ISO, which were inhibited by co-treatment with the β-adrenergic antagonist propranolol (Pro) (FIG. 2a). A maximum response of 24.1%±2.7% was obtained with Fsk stimulation in the presence of 100 μM 3-isobutyl-1-methylxanthine IBMX), a phosphodiesterase (PDE) inhibitor (FIG. 2c). This ICUE assay had a Z' factor of 0.51, an S/N ratio of 17.8, and a CV of 12%. Possible sources of the variation and reduced signal are transfection efficiency and expression variability. Experiments using a stable cell line showed significant improvement of the assay, indicated by a maximum response of 43.3%±2.3% and a Z' factor of 0.78.

EXAMPLE 6

Parallel Kinetic Profiling

This example demonstrates parallel kinetic profiling of a panel of agonists and antagonists and reveals their differential effects on PKA activity and cAMP dynamics.

As shown in FIG. 2, ISO-induced responses can be inhibited by 10 μM Pro, which had no effect on Fsk-stimulated responses. Supplementing IBMX sustained responses and increased their amplitude, indicating that PDEs play an important role in switching off cAMP/PKA signaling. Addition of H89, a PKA inhibitor, diminished the Fsk-stimulated response of AKAR3 but not that of ICUE3 (FIGS. 2c and 2d). Interestingly, H89 increased the ICUE3 response, similar to the effect caused by the combination of Fsk and IBMX (FIG. 2c). This finding was confirmed with single cell imaging and suggests that disruption of a feedback loop possibly involving PKA-dependent activation of PDE and/or inhibition of adenylyl cyclase could directly contribute to enhanced cAMP accumulation. Thus, use of these assays allows parallel evaluation of key targets in the same signaling pathway and can facilitate understanding of complex drug effects.

EXAMPLE 7

High-Throughput Screening of a Clinical Compound Library

In a primary screening, 160 compounds from the Johns Hopkins Clinical Compound Library were added to AKAR3-expressing HEK-293 cells in individual wells of 96-well plates to a final concentration of 10 µM after a base line reading. Time courses were recorded to monitor any fluorescence changes upon drug addition and to identify hits which activate PKA as potential agonists. A standard agonist, e.g., ISO, was then added to all wells, and changes of emission ratios were calculated to identify compounds which inhibit such changes as potential antagonists.

Screening using cells which stably express ICUE was performed in 96-well plates in a similar fashion. Both agonists and antagonists were identified in one primary screening, and some kinetic information can be obtained which facilitates early and direct characterization of hits.

Figure 3A:
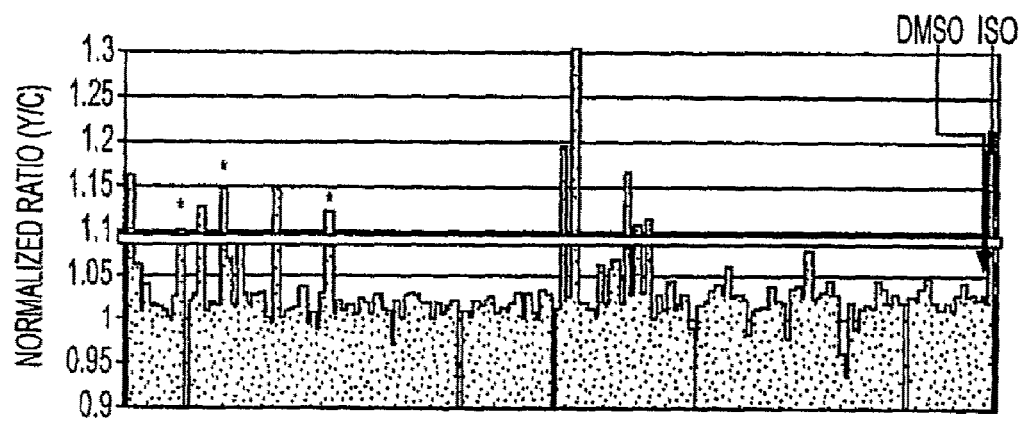
FIG. 3A, normalized emission ratio (yellow/cyan) from cells expressing AKAR3 treated with individual library compounds, compared to the negative control in which only buffer was added and the positive control in which ISO (250 nM) was added (agonist screen). Individual bars along the X axis represent individual library compounds. The asterisks indicate responses of ritrodrine, ISO, and epinephrine.
Figure 3B:
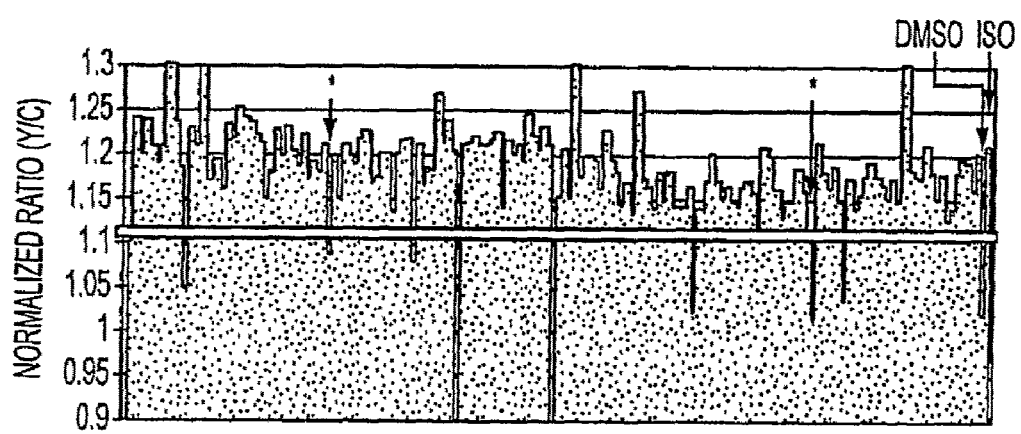
FIG. 3B, normalized emission ratio (yellow/cyan) from cells expressing AKAR3 first treated with individual library compounds for about 15 minutes, then stimulated by ISO (250 nM) (antagonist screen). The positive control in which only ISO was added and the negative control in which only buffer was added are shown as labeled. Individual bars along the X axis represent individual library compounds. The asterisks indicate responses from epinephrine and propranolol treated cells in response to ISO.

As shown in FIGS. 3a and 3b, most drugs caused no stimulation or inhibition of AKAR responses. In some cases, abnormal fluorescence changes were observed upon addition of compounds to the cells, which correlated with their fluorescent or colorimetric properties or toxicity. Potential agonists were identified by selecting compounds which stimulated emission ratio changes larger than 6 times the standard deviation above the negative control (FIG. 3a).

Figure 3C:
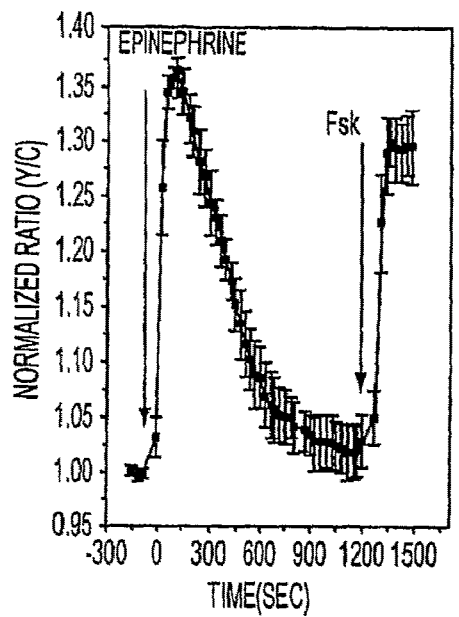
FIG. 3C, representative time courses of emission ratio (yellow/cyan) change of cells expressing AKAR3 treated with 10 μM epinephrine followed by 50 μM FSK in single-cell imaging experiments. Error bars represent standard deviation (n=3).
Figure 3D:
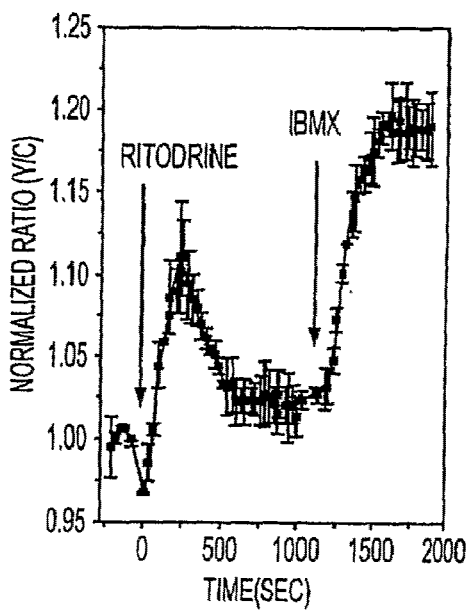
FIG. 3D, representative time courses of emission ratio (yellow/cyan) change of cells expressing AKAR3 treated with 50 μM ritodrine followed by 100 μM 3-isobutyl-1-methylxanthine (IBMX) in single-cell imaging experiments. Error bars represent standard deviation (n=2).

Three such compounds that stimulated AKAR responses on their own without generating abnormal fluorescence changes in individual channels were identified as ISO, ritodrine, and epinephrine. ISO is a general β-adrenergic agonist. Epinephrine, another well-known adrenergic agonist, activates both β-adrenergic receptors (β-AR) and α-adrenergic receptors. In β2AR-expressing HEK-293 cells, 10 µM epinephrine stimulates cAMP production and PKA activation, as confirmed by single cell imaging experiments (FIG. 3c). On the other hand, the β32AR-specific agonist ritodrine stimulated a moderate and gradual response in HEK-293 cells expressing AKAR3 when tested in single cell imaging (FIG. 3d). This small response could be enhanced by blocking PDE activity with IBMX (FIG. 3d), while IBMX alone did not generate any AKAR responses in HEK-293 cells.

One compound potently inhibited the ISO-stimulated responses in both AKAR and ICUE assays and was identified to be propranolol. Epinephrine also was identified as a hit in the antagonist category, indicating that after inducing a transient response (FIG. 3c), continuous presence of epinephrine decreased the cell response to subsequent stimulation by ISO.

Figure 3E:
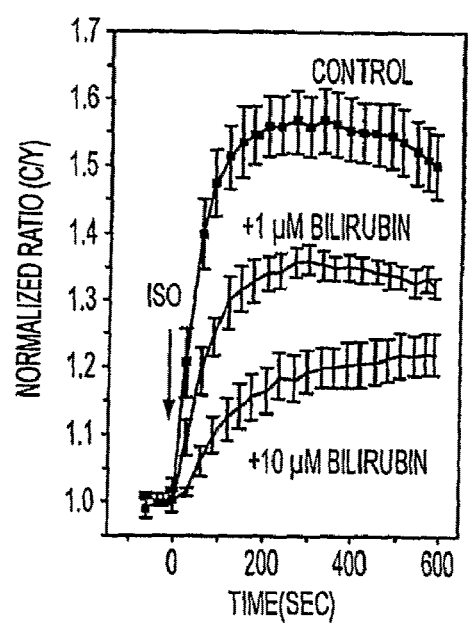
FIG. 3E, representative time courses of emission ratio (yellow/cyan) change of ICUE pretreated with bilirubin (1 μM and 10 μM) followed by ISO stimulation in the presence of IBMX. Error bars represent standard deviation (n=22, 9, and 10).

An additional potential antagonist was identified from the ICUE assay. The inhibitory effects of this compound, bilirubin, were verified in single cell imaging experiments. As shown in FIG. 3e, the ISO-stimulated ICUE response was inhibited by 40% by 1 µM bilirubin, and the inhibition was more than 60% by 10 µM bilirubin. Although bilirubin has been shown to be a protective antioxidant, very high levels can lead to its accumulation in the brain, causing kernicterus. The ability of bilirubin to inhibit PKA in vitro at tens of µM was suggested to play a role in the neurotoxic effects of bilirubin in patients with kernicterus. Our results suggest an alternative mechanism of inhibition of PKA by bilirubin, i.e., through inhibition of cellular cAMP production.

The ICUE assay may be more sensitive for identify potential antagonists, while the AKAR assay is more sensitive for agonists, as an amplification step is incorporated in the AKAR assay when a single active PKA molecule phosphorylates multiple AKAR substrates.

The invention claimed is:

1. A protein kinase A (PKA) reporter, comprising from N to C terminus:
   (a) a cerulean fluorescent protein;
   (b) a forkhead associated domain 1 (FHA1) covalently linked to the cerulean protein with an amino acid linker Arg-Met-His;
   (c) the amino acid sequence SEQ ID NO:3 covalently linked to the FHA1; and
   (d) a circularly permuted variant of yellow fluorescent protein covalently linked to the amino acid sequence SEQ ID NO:3.

2. The PKA reporter of claim 1 which comprises the amino acid sequence SEQ ID NO:4.

3. The PKA reporter of claim 1 which comprises a subcellular targeting sequence.

4. The PKA reporter of claim 3 wherein the subcellular targeting sequence which targets the reporter to a subcellular location selected from the group consisting of a plasma membrane, a nuclear membrane, a cytosol, an endoplasmic reticulum, a mitochondria, a mitochondrial matrix, a chloroplast, a medial trans-Golgi cisternae, a lumen of a lysosome, and a lumen of an endosome.

5. The PKA reporter of claim 3 which comprises a subcellular targeting sequence selected from the group consisting of a plasma membrane targeting sequence comprising SEQ ID NO:12, a nuclear localization signal sequence comprising SEQ ID NO:13, a mitochondrial localization sequence comprising SEQ ID NO:14, and a mitochondrial matrix targeting signal comprising SEQ ID NO:15.

6. A method for detecting a change in PKA activity, comprising:
   detecting a first resonance energy transfer of the PKA reporter of claim 1 at a first time point;
   detecting a second resonance energy transfer of the PKA reporter at a second time point; and
   comparing the first and the second resonance energy transfers, wherein a difference between the first and the second resonance energy transfers reflects the change in PKA activity.

7. The method of claim 6 wherein the first and second resonance energy transfers are detected by determining a property selected from the group consisting of a quantum efficiency, an excitation spectrum, an emission spectrum, an excitation wavelength maximum, an emission wavelength maximum, a ratio of excitation amplitudes at two wavelengths, a ratio of emission amplitudes at two wavelengths, an excited state lifetime, anisotropy, a polarization of emitted light, resonance energy transfer, and a quenching of emission at a wavelength.

8. The method of claim 6 wherein the PKA reporter is in a cell-free system.

9. The method of claim 6 wherein the PKA reporter is in a an isolated cell.

10. The method of claim 9 wherein the cell is in an isolated tissue sample.

11. The method of claim 9 wherein the cell is in ft an isolated whole organ.

12. The method of claim 9 wherein the cell is in a well of a multi-well plate.

13. The method of claim 12 wherein each of a plurality of wells of the multi-well plate comprises a cell which comprises the PKA reporter.

14. The method of claim 13 further comprising contacting each well of the plurality with a different test compound and determining resonance energy transfers in the presence of the different test compounds.

15. The method of claim 6 further comprising determining the resonance energy transfer in the presence of a test compound.

16. The method of claim 6 wherein the first and second resonance energy transfers are detected using fluorescence activated cell sorting.

17. The method of claim 6 further comprising detecting a cAMP concentration.

18. A kit, comprising: (a) the PKA reporter of claim 1; and (b) instructions for use of the PKA reporter.

19. The kit of claim 18 further comprising a cAMP reporter.

* * * * *

SEQUENCE LISTING

```
<160> NUMBER OF SEQ ID NOS: 27

<210> SEQ ID NO 1
<211> LENGTH: 647
<212> TYPE: PRT
<213> ORGANISM: Artificial Sequence
<220> FEATURE:
<223> OTHER INFORMATION: AKAR3 reporter

<400> SEQUENCE: 1

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

-continued

```
Val Lys Phe Glu Gly Asp Thr Leu Val Asn Arg Ile Glu Leu Lys Gly
            115                 120                 125
Ile Asp Phe Lys Glu Asp Gly Asn Ile Leu Gly His Lys Leu Glu Tyr
        130                 135                 140
Asn Tyr Ile Ser His Asn Val Tyr Ile Thr Ala Asp Lys Gln Lys Asn
145                 150                 155                 160
Gly Ile Lys Ala His Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
210                 215                 220
Val Thr Ala Ala Arg Met His Lys Phe Ser Gln Gln Ile Gly Glu
225                 230                 235                 240
Asn Ile Val Cys Arg Val Ile Cys Thr Thr Gly Gln Ile Pro Ile Arg
                245                 250                 255
Asp Leu Ser Ala Asp Ile Ser Gln Val Leu Lys Glu Lys Arg Ser Ile
            260                 265                 270
Lys Lys Val Trp Thr Phe Gly Arg Asn Pro Ala Cys Asp Tyr His Leu
        275                 280                 285
Gly Asn Ile Ser Arg Leu Ser Asn Lys His Phe Gln Ile Leu Leu Gly
        290                 295                 300
Glu Asp Gly Asn Leu Leu Leu Asn Asp Ile Ser Thr Asn Gly Thr Trp
305                 310                 315                 320
Leu Asn Gly Gln Lys Val Glu Lys Asn Ser Asn Gln Leu Leu Ser Gln
                325                 330                 335
Gly Asp Glu Ile Thr Val Gly Val Gly Val Glu Ser Asp Ile Leu Ser
            340                 345                 350
Leu Val Ile Phe Ile Asn Asp Lys Phe Lys Gln Cys Leu Glu Gln Asn
        355                 360                 365
Lys Val Asp Arg Ser Ala Gly Lys Pro Gly Ser Gly Glu Gly Ser Thr
370                 375                 380
Lys Gly Leu Arg Arg Ala Thr Leu Val Asp Gly Thr Gly Ser
385                 390                 395                 400
Glu Leu Met Gly Gly Val Gln Leu Ala Asp His Tyr Gln Gln Asn Thr
                405                 410                 415
Pro Ile Gly Asp Gly Pro Val Leu Leu Pro Asp Asn His Tyr Leu Ser
            420                 425                 430
Tyr Gln Ser Lys Leu Ser Lys Asp Pro Asn Glu Lys Arg Asp His Met
        435                 440                 445
Val Leu Leu Glu Phe Val Thr Ala Ala Gly Ile Thr Leu Gly Met Asp
        450                 455                 460
Glu Leu Tyr Lys Gly Gly Thr Gly Gly Ser Met Val Ser Lys Gly Glu
465                 470                 475                 480
Glu Leu Phe Thr Gly Val Val Pro Ile Leu Val Glu Leu Asp Gly Asp
                485                 490                 495
Val Asn Gly His Lys Phe Ser Val Ser Gly Glu Gly Glu Gly Asp Ala
            500                 505                 510
Thr Tyr Gly Lys Leu Thr Leu Lys Leu Ile Cys Thr Thr Gly Lys Leu
        515                 520                 525
Pro Val Pro Trp Pro Thr Leu Val Thr Thr Leu Gly Tyr Gly Leu Gln
        530                 535                 540
```

-continued

Cys Phe Ala Arg Tyr Pro Asp His Met Lys Gln His Asp Phe Phe Lys
545                 550                 555                 560

Ser Ala Met Pro Glu Gly Tyr Val Gln Glu Arg Thr Ile Phe Phe Lys
                565                 570                 575

Asp Asp Gly Asn Tyr Lys Thr Arg Ala Glu Val Lys Phe Glu Gly Asp
            580                 585                 590

Thr Leu Val Asn Arg Ile Glu Leu Lys Gly Ile Asp Phe Lys Glu Asp
        595                 600                 605

Gly Asn Ile Leu Gly His Lys Leu Glu Tyr Asn Tyr Asn Ser His Asn
    610                 615                 620

Val Tyr Ile Thr Ala Asp Lys Gln Lys Asn Gly Ile Lys Ala Asn Phe
625                 630                 635                 640

Lys Ile Arg His Asn Ile Glu
            645

<210> SEQ ID NO 2
<211> LENGTH: 1944
<212> TYPE: DNA
<213> ORGANISM: Artificial Sequence
<220> FEATURE:
<223> OTHER INFORMATION: AKAR3 reporter
<220> FEATURE:
<221> NAME/KEY: misc_feature
<222> LOCATION: 1278
<223> OTHER INFORMATION: n = A,T,C or G

<400> SEQUENCE: 2

```
atggtgagca agggcgagga gctgttcacc ggggtggtgc ccatcctggt cgagctggac      60
ggcgacgtaa acggccacag gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcagcc gctacccoga ccacatgaag     240
cagcacgact tcttcaagtc cgccatgccc gaaggctacg tccaggagcg taccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg cccacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgcccgcatg cataagtttt ctcaagaaca gatcggcgaa     720
aacattgtgt gcagggtcat tgtaccacg ggtcaaattc catccgaga tttgtcagct     780
gatatttcac aagtgcttaa ggaaaaacga tccataaaga agtttggac atttggtaga     840
aacccagcct gtgactatca tttaggaaac atttcaagac tgtcaaataa gcatttccaa     900
atactactag gagaagacgg taaccttta ttgaatgaca tttccactaa tgggacctgg     960
ttaaatgggc aaaagtcga gaagaacagc aatcagttac tgtctcaagg tgatgaaata    1020
accgttggtg taggcgtgga atcagatatt ttatctctgg tcattttcat aaacgacaaa    1080
tttaagcagt gcctcgagca gaacaaagtt gatcgctctg caggtaagcc aggcagcggc    1140
gagggcagca ccaagggcct cgtcgcgcc accctggtgg acggcggcac cggcggcagc    1200
gagctcatgg gcggcgtgca gctcgccgac cactaccagc agaacacccc catcggcgac    1260
ggccccgtgc tgctgccnga caaccactac ctgagctacc agtccaagct gagcaaagac    1320
```

```
cccaacgaga agcgcgatca catggtcctg ctggagttcg tgaccgccgc cgggatcact   1380
ctcggcatgg acgagctgta caagggaggt accggtggat ctatggtgag caagggcgag   1440
gagctgttca ccggggtggt gcccatcctg gtcgagctgg acggcgacgt aaacggccac   1500
aagttcagcg tgtccggcga gggcgagggc gatgccacct acggcaagct gaccctgaag   1560
ctgatctgca ccaccggcaa gctgcccgtg ccctggccca ccctcgtgac caccctgggc   1620 tacggcttc agtgcttcgc ccgctacccc gaccacatga gcagcacga cttcttcaag    1680 tccgccatgc ccgaaggcta cgtccaggag cgcaccatct tcttcaagga cgacggcaac   1740
tacaagaccc gcgccgaggt gaagttcgag ggcgacaccc tggtgaaccg catcgagctg   1800
aagggcatcg acttcaagga ggacggcaac atcctggggc acaagctgga gtacaactac   1860
aacagccaca cgtctatat caccgccgac aagcagaaga cggcatcaa ggccaacttc     1920 aagatccgcc acaacatcga gtaa                                          1944
```

<210> SEQ ID NO 3
<211> LENGTH: 30
<212> TYPE: PRT
<213> ORGANISM: Artificial Sequence
<220> FEATURE:
<223> OTHER INFORMATION: domain of AKAR3 reporter

<400> SEQUENCE: 3

```
Ala Gly Thr Lys Pro Gly Ser Gly Glu Gly Ser Thr Lys Gly Leu Arg
 1               5                   10                  15

Arg Ala Thr Leu Val Asp Gly Gly Thr Gly Gly Ser Glu Leu
             20                  25                  30
```

<210> SEQ ID NO 4
<211> LENGTH: 689
<212> TYPE: PRT
<213> ORGANISM: Artificial Sequence
<220> FEATURE:
<223> OTHER INFORMATION: AKAR3.2 reporter

<400> SEQUENCE: 4

```
His His His His His His Gly Met Ala Ser Met Thr Gly Gly Gln Gln
 1               5                   10                  15

Met Gly Arg Asp Leu Tyr Asp Asp Asp Lys Asp Pro Met Val Ser
             20                  25                  30

Lys Gly Glu Glu Leu Phe Thr Gly Val Val Pro Ile Leu Val Glu Leu
                 35                  40                  45

Asp Gly Asp Val Asn Gly His Arg Phe Ser Val Ser Gly Glu Gly Glu
     50                  55                  60

Gly Asp Ala Thr Tyr Gly Lys Leu Thr Leu Lys Phe Ile Cys Thr Thr
65                  70                  75                  80

Gly Lys Leu Pro Val Pro Trp Pro Thr Leu Val Thr Thr Leu Thr Trp
                 85                  90                  95

Gly Val Gln Cys Phe Ala Arg Tyr Pro Asp His Met Lys Gln His Asp
                100                 105                 110

Phe Phe Lys Ser Ala Met Pro Glu Gly Tyr Val Gln Glu Arg Thr Ile
            115                 120                 125

Phe Phe Lys Asp Asp Gly Asn Tyr Lys Thr Arg Ala Glu Val Lys Phe
        130                 135                 140

Glu Gly Asp Thr Leu Val Asn Arg Ile Glu Leu Lys Gly Ile Asp Phe
145                 150                 155                 160

Lys Glu Asp Gly Asn Ile Leu Gly His Lys Leu Glu Tyr Asn Ala Ile
                165                 170                 175
```

```
Ser Asp Asn Val Tyr Ile Thr Ala Asp Lys Gln Lys Asn Gly Ile Lys
            180                 185                 190

Ala His Phe Lys Ile Arg His Asn Ile Glu Asp Gly Ser Val Gln Leu
            195                 200                 205

Ala Asp His Tyr Gln Gln Asn Thr Pro Ile Gly Asp Gly Pro Val Leu
        210                 215                 220

Leu Pro Asp Asn His Tyr Leu Ser Thr Gln Ser Ala Leu Ser Lys Asp
225                 230                 235                 240

Pro Asn Glu Lys Arg Asp His Met Val Leu Leu Glu Phe Val Thr Ala
                245                 250                 255

Ala Gly Ile Thr Leu Gly Met Asp Glu Leu Tyr Lys Arg Met His Lys
            260                 265                 270

Phe Ser Gln Glu Gln Ile Gly Glu Asn Ile Val Cys Arg Val Ile Cys
            275                 280                 285

Thr Thr Gly Gln Ile Pro Ile Arg Asp Leu Ser Ala Asp Ile Ser Gln
        290                 295                 300

Val Leu Lys Glu Lys Arg Ser Ile Lys Lys Val Trp Thr Phe Gly Arg
305                 310                 315                 320

Asn Pro Ala Cys Asp Tyr His Leu Gly Asn Ile Ser Arg Leu Ser Asn
                325                 330                 335

Lys His Phe Gln Ile Leu Leu Gly Glu Asp Gly Asn Leu Leu Leu Asn
            340                 345                 350

Asp Ile Ser Thr Asn Gly Thr Trp Leu Asn Gly Gln Lys Val Glu Lys
            355                 360                 365

Asn Ser Asn Gln Leu Leu Ser Gln Gly Asp Glu Ile Thr Val Gly Val
        370                 375                 380

Gly Val Glu Ser Asp Ile Leu Ser Leu Val Ile Phe Ile Asn Asp Lys
385                 390                 395                 400

Phe Lys Gln Cys Leu Glu Gln Asn Lys Val Asp Arg Ser Ala Gly Lys
                405                 410                 415

Pro Gly Ser Gly Glu Gly Ser Thr Lys Gly Leu Arg Arg Ala Thr Leu
            420                 425                 430

Val Asp Gly Gly Thr Gly Gly Ser Glu Leu Met Gly Gly Val Gln Leu
        435                 440                 445

Ala Asp His Tyr Gln Gln Asn Thr Pro Ile Gly Asp Gly Pro Val Leu
        450                 455                 460

Leu Pro Asp Asn His Tyr Leu Ser Tyr Gln Ser Lys Leu Ser Lys Asp
465                 470                 475                 480

Pro Asn Glu Lys Arg Asp His Met Val Leu Leu Glu Phe Val Thr Ala
                485                 490                 495

Ala Gly Ile Thr Leu Gly Met Asp Glu Leu Tyr Lys Gly Gly Thr Gly
            500                 505                 510

Gly Ser Met Val Ser Lys Gly Glu Glu Leu Phe Thr Gly Val Val Pro
        515                 520                 525

Ile Leu Val Glu Leu Asp Gly Asp Val Asn Gly His Lys Phe Ser Val
530                 535                 540

Ser Gly Glu Gly Glu Gly Asp Ala Thr Tyr Gly Lys Leu Thr Leu Lys
545                 550                 555                 560

Leu Ile Cys Thr Thr Gly Lys Leu Pro Val Pro Trp Pro Thr Leu Val
                565                 570                 575

Thr Thr Leu Gly Tyr Gly Leu Gln Cys Phe Ala Arg Tyr Pro Asp His
            580                 585                 590

Met Lys Gln His Asp Phe Phe Lys Ser Ala Met Pro Glu Gly Tyr Val
```

-continued

```
                595              600              605
Gln Glu Arg Thr Ile Phe Phe Lys Asp Asp Gly Asn Tyr Lys Thr Arg
        610              615              620

Ala Glu Val Lys Phe Glu Gly Asp Thr Leu Val Asn Arg Ile Glu Leu
625              630              635              640

Lys Gly Ile Asp Phe Lys Glu Asp Gly Asn Ile Leu Gly His Lys Leu
            645              650              655

Glu Tyr Asn Tyr Asn Ser His Asn Val Tyr Ile Thr Ala Asp Lys Gln
            660              665              670

Lys Asn Gly Ile Lys Ala Asn Phe Lys Ile Arg His Asn Ile Glu Glu
            675              680              685

Phe

<210> SEQ ID NO 5
<211> LENGTH: 2070
<212> TYPE: DNA
<213> ORGANISM: Artificial Sequence
<220> FEATURE:
<223> OTHER INFORMATION: AKAR3.2 reporter
<220> FEATURE:
<221> NAME/KEY: misc_feature
<222> LOCATION: 1398
<223> OTHER INFORMATION: n = A,T,C or G

<400> SEQUENCE: 5
catcatcatc atcatcatgg tatggctagc atgactggtg acagcaaat  gggtcgggat        60 ctgtacgacg atgacgataa ggatcccatg gtgagcaagg gcgaggagct gttcaccggg       120
gtggtgccca tcctggtcga gctggacggc gacgtaaacg ccacaggtt  cagcgtgtcc       180 ggcgagggcg agggcgatgc cacctacggc aagctgaccc tgaagttcat ctgcaccacc       240
ggcaagctgc ccgtgccctg gcccaccctc gtgaccaccc tgacctgggg cgtgcagtgc       300
ttcgcccgct accccgacca catgaagcag cacgacttct tcaagtccgc catgcccgaa       360
ggctacgtcc aggagcgtac catcttcttc aaggacgacg gcaactacaa gacccgcgcc       420
gaggtgaagt tcgagggcga caccctggtg aaccgcatcg agctgaaggg catcgacttc       480
aaggaggacg gcaacatcct ggggcacaag ctggagtaca actaccatcag tgacaacgtc       540 tatatcaccg ccgacaagca gaagaacggc atcaaggccc acttcaagat ccgccacaac       600
atcgaggacg gcagcgtgca gctcgccgac cactaccagc agaacacccc catcggcgac       660
ggccccgtgc tgctgcccga caaccactac ctgagcaccc agtccgccct gagcaaagac       720
cccaacgaga agcgcgatca catggtcctg ctggagttcg tgaccgccgc cgggatcact       780
ctcggcatgg acgagctgta caagcgcatg cataagtttt ctcaagaaca gatcggcgaa       840
aacattgtgt gcagggtcat ttgtaccacg ggtcaaattc ccatccgaga tttgtcagct       900
gatatttcac aagtgcttaa ggaaaaacga tccataaaga agtttggac  atttggtaga       960 aacccagcct gtgactatca tttaggaaac atttcaagac tgtcaaataa gcatttccaa      1020
atactactag gagaagacgg taaccttta  ttgaatgaca tttccactaa tgggacctgg      1080
ttaaatgggc aaaagtcga  gaagaacagc aatcagttac tgtctcaagg tgatgaaata      1140
accgttggtg taggcgtgga atcagatatt ttatctctgg tcattttcat aaacgacaaa      1200
tttaagcagt gcctcgagca gaacaaagtt gatcgctctg caggtaagcc aggcagcggc      1260
gagggcagca ccaagggcct cgtcgcgcc  accctggtgg acggcggcac cggcggcagc      1320
gagctcatgg gcggcgtgca gctcgccgac cactaccagc agaacacccc catcggcgac      1380
ggccccgtgc tgctgccnga caaccactac ctgagctacc agtccaagct gagcaaagac      1440
```

-continued

```
cccaacgaga agcgcgatca catggtcctg ctggagttcg tgaccgccgc cgggatcact      1500
ctcggcatgg acgagctgta caagggaggt accggtggat ctatggtgag caagggcgag      1560
gagctgttca ccggggtggt gcccatcctg gtcgagctgg acggcgacgt aaacggccac      1620
aagttcagcg tgtccggcga gggcgagggc gatgccacct acggcaagct gaccctgaag      1680
ctgatctgca ccaccggcaa gctgcccgtg ccctggccca ccctcgtgac cacccctgggc     1740 tacggccttc agtgcttcgc ccgctacccc gaccacatga agcagcacga cttcttcaag      1800
tccgccatgc ccgaaggcta cgtccaggag cgcaccatct tcttcaagga cgacggcaac      1860
tacaagaccc gcgccgaggt gaagttcgag ggcgacaccc tggtgaaccg catcgagctg      1920
aagggcatcg acttcaagga ggacggcaac atcctggggc acaagctgga gtacaactac      1980
aacagccaca acgtctatat caccgccgac aagcagaaga cggcatcaa ggccaacttc       2040 aagatccgcc acaacatcga gtaagaattc                                       2070
```

<210> SEQ ID NO 6
<211> LENGTH: 225
<212> TYPE: PRT
<213> ORGANISM: Discosoma

<400> SEQUENCE: 6

```
Met Arg Ser Ser Lys Asn Val Ile Lys Glu Phe Met Arg Phe Lys Val
 1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225
```

<210> SEQ ID NO 7
<211> LENGTH: 18
<212> TYPE: PRT

<213> ORGANISM: Artificial Sequence
<220> FEATURE:
<223> OTHER INFORMATION: linker

<400> SEQUENCE: 7

Gly Ser Thr Ser Gly Ser Gly Lys Pro Gly Ser Gly Glu Gly Ser Thr
1               5                   10                  15
Lys Gly

<210> SEQ ID NO 8
<211> LENGTH: 238
<212> TYPE: PRT
<213> ORGANISM: Aequora

<400> SEQUENCE: 8

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 9
<211> LENGTH: 239
<212> TYPE: PRT
<213> ORGANISM: Aequora

<400> SEQUENCE: 9

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

```
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 10
<211> LENGTH: 239
<212> TYPE: PRT
<213> ORGANISM: Aequora

<400> SEQUENCE: 10

Met Val Ser Lys Gly Glu Glu Leu Phe Thr Gly Val Val Pro Ile Leu
  1               5                  10                  15

Val Glu Leu Asp Gly Asp Val Asn Gly His Arg Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

```
Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 11
<211> LENGTH: 239
<212> TYPE: PRT
<213> ORGANISM: Aequora

<400> SEQUENCE: 11

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Lys Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 12
<211> LENGTH: 10
<212> TYPE: PRT
<213> ORGANISM: Homo sapiens

<400> SEQUENCE: 12

Pro Lys Lys Lys Arg Lys Val Glu Asp Ala
1               5                   10

<210> SEQ ID NO 13
<211> LENGTH: 13
<212> TYPE: PRT
<213> ORGANISM: Homo sapiens
```

```
<400> SEQUENCE: 13

Lys Lys Lys Lys Ser Lys Thr Lys Cys Val Ile Met
1               5                   10

<210> SEQ ID NO 14
<211> LENGTH: 30
<212> TYPE: PRT
<213> ORGANISM: Homo sapiens

<400> SEQUENCE: 14

Met Ala Ile Gln Leu Arg Ser Leu Phe Pro Leu Ala Leu Pro Gly Met
1               5                   10                  15

Leu Ala Leu Leu Gly Trp Trp Trp Phe Ser Arg Lys Lys
            20                  25                  30

<210> SEQ ID NO 15
<211> LENGTH: 16
<212> TYPE: PRT
<213> ORGANISM: Homo sapiens

<400> SEQUENCE: 15

Met Leu Ser Leu Arg Gly Ser Ile Arg Phe Lys Arg Ser Gly Ile
1               5                   10                  15

<210> SEQ ID NO 16
<211> LENGTH: 6
<212> TYPE: PRT
<213> ORGANISM: Artificial Sequence
<220> FEATURE:
<223> OTHER INFORMATION: linker
<220> FEATURE:
<221> NAME/KEY: VARIANT
<222> LOCATION: 3, 4
<223> OTHER INFORMATION: Xaa = Any Amino Acid

<400> SEQUENCE: 16

Cys Cys Xaa Xaa Cys Cys
1               5

<210> SEQ ID NO 17
<211> LENGTH: 9
<212> TYPE: PRT
<213> ORGANISM: Homo sapiens

<400> SEQUENCE: 17

Leu Pro Pro Leu Glu Arg Leu Thr Leu
1               5

<210> SEQ ID NO 18
<211> LENGTH: 636
<212> TYPE: PRT
<213> ORGANISM: Artificial Sequence
<220> FEATURE:
<223> OTHER INFORMATION: GRet_AKAR

<400> SEQUENCE: 18

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60
```

```
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Arg Met His Lys Phe Ser Gln Glu Gln Ile Gly Glu
225                 230                 235                 240

Asn Ile Val Cys Arg Val Ile Cys Thr Thr Gly Gln Ile Pro Ile Arg
                245                 250                 255

Asp Leu Ser Ala Asp Ile Ser Gln Val Leu Lys Glu Lys Arg Ser Ile
            260                 265                 270

Lys Lys Val Trp Thr Phe Gly Arg Asn Pro Ala Cys Asp Tyr His Leu
        275                 280                 285

Gly Asn Ile Ser Arg Leu Ser Asn Lys His Phe Gln Ile Leu Leu Gly
    290                 295                 300

Glu Asp Gly Asn Leu Leu Leu Asn Asp Ile Ser Thr Asn Gly Thr Trp
305                 310                 315                 320

Leu Asn Gly Gln Lys Val Glu Lys Asn Ser Asn Gln Leu Leu Ser Gln
                325                 330                 335

Gly Asp Glu Ile Thr Val Gly Val Gly Val Glu Ser Asp Ile Leu Ser
            340                 345                 350

Leu Val Ile Phe Ile Asn Asp Lys Phe Lys Gln Cys Leu Glu Gln Asn
        355                 360                 365

Lys Val Asp Arg Ser Ala Gly Lys Pro Gly Ser Gly Glu Gly Ser Thr
    370                 375                 380

Lys Gly Leu Arg Arg Ala Thr Leu Val Asp Gly Thr Gly Gly Gly Ser
385                 390                 395                 400

Glu Leu Met Val Ser Lys Gly Glu Glu Asp Asn Met Ala Ile Ile Lys
                405                 410                 415

Glu Phe Met Arg Phe Lys Val His Met Glu Gly Ser Val Asn Gly His
            420                 425                 430

Glu Phe Glu Ile Glu Gly Glu Gly Glu Gly Arg Pro Tyr Glu Gly Thr
        435                 440                 445

Gln Thr Ala Lys Leu Lys Val Thr Lys Gly Gly Pro Leu Pro Phe Ala
    450                 455                 460

Trp Asp Ile Leu Ser Pro Gln Phe Met Tyr Gly Ser Lys Ala Tyr Val
465                 470                 475                 480

Lys His Pro Ala Asp Ile Pro Asp Tyr Leu Lys Leu Ser Phe Pro Glu
                485                 490                 495
```

```
Gly Phe Lys Trp Glu Arg Val Met Asn Phe Glu Asp Gly Val Val
                500                 505                 510
Thr Val Thr Gln Asp Ser Ser Leu Gln Asp Gly Glu Phe Ile Tyr Lys
            515                 520                 525
Val Lys Leu Arg Gly Thr Asn Phe Pro Ser Asp Gly Pro Val Met Gln
        530                 535                 540
Lys Lys Thr Met Gly Trp Glu Ala Ser Ser Met Tyr Pro Glu Asp Gly
545                 550                 555                 560
Ala Leu Lys Gly Glu Ile Lys Gln Arg Leu Lys Leu Lys Asp Gly Gly
                565                 570                 575
His Tyr Asp Ala Glu Val Lys Thr Thr Tyr Lys Ala Lys Lys Pro Val
            580                 585                 590
Gln Leu Pro Gly Ala Tyr Asn Val Asn Ile Lys Leu Asp Ile Thr Ser
        595                 600                 605
His Asn Glu Asp Tyr Thr Ile Val Glu Gln Tyr Glu Arg Ala Glu Gly
610                 615                 620
Arg His Ser Thr Gly Gly Met Asp Glu Leu Tyr Lys
625                 630                 635

<210> SEQ ID NO 19
<211> LENGTH: 1917
<212> TYPE: DNA
<213> ORGANISM: Artificial Sequence
<220> FEATURE:
<223> OTHER INFORMATION: GRet_AKAR

<400> SEQUENCE: 19
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgcccgcatg cataagtttt ctcaagaaca gatcggcgaa     720
aacattgtgt gcagggtcat tgtaccacgg gtcaaattc catccgaga tttgtcagct     780
gatatttcac aagtgcttaa ggaaaaacga tccataaaga aagtttggac atttggtaga     840
aacccagcct gtgactatca tttaggaaac atttcaagac tgtcaaataa gcatttccaa     900
atactactag agaagacgg taaccttta ttgaatgaca tttccactaa tgggacctgg     960
ttaaatgggc aaaaagtcga agaacagc aatcagttac tgtctcaagg tgatgaaata    1020
accgttggtg taggcgtgga atcagatatt ttatctctgg tcattttcat aaacgacaaa    1080
tttaagcagt gcctcgagca gaacaaagtt gatcgctctg caggtaagcc aggcagcggc    1140
gagggcagca ccaagggcct gcgtcgcgcc accctggtgg acggcggcac cggcggcagc    1200
gagctcatgg tgagcaaggg cgaggaggat aacatggcca tcatcaagga gttcatgcgc    1260
```

-continued

```
ttcaaggtgc acatggaggg ctccgtgaac ggccacgagt tcgagatcga gggcgagggc   1320
gagggccgcc cctacgaggg cacccagacc gccaagctga aggtgaccaa gggtggcccc   1380
ctgcccttcg cctgggacat cctgtcccct cagttcatgt acggctccaa ggcctacgtg   1440
aagcaccccg ccgacatccc cgactacttg aagctgtcct tccccgaggg cttcaagtgg   1500
gagcgcgtga tgaacttcga ggacggcggc gtggtgaccg tgacccagga ctcctccctg   1560
caggacggcg agttcatcta caaggtgaag ctgcgcggca ccaacttccc ctccgacggc   1620
cccgtaatgc agaagaagac catgggctgg gaggcctcct ccgagcggat gtaccccgag   1680
gacggcgccc tgaagggcga gatcaagcag aggctgaagc tgaaggacgg cggccactac   1740
gacgctgagg tcaagaccac ctacaaggcc aagaagcccg tgcagctgcc cggcgcctac   1800
aacgtcaaca tcaagttgga catcacctcc cacaacgagg actacaccat cgtggaacag   1860
tacgaacgcg ccgagggccg ccactccacc ggcggcatgg acgagctgta caagtaa      1917
```

<210> SEQ ID NO 20
<211> LENGTH: 7
<212> TYPE: PRT
<213> ORGANISM: Artificial Sequence
<220> FEATURE:
<223> OTHER INFORMATION: protein kinase A substrate

<400> SEQUENCE: 20

Leu Arg Arg Ala Ser Leu Pro
 1               5

<210> SEQ ID NO 21
<211> LENGTH: 7
<212> TYPE: PRT
<213> ORGANISM: Artificial Sequence
<220> FEATURE:
<223> OTHER INFORMATION: protein kinase A substrate

<400> SEQUENCE: 21

Leu Arg Arg Ala Thr Leu Pro
 1               5

<210> SEQ ID NO 22
<211> LENGTH: 6
<212> TYPE: PRT
<213> ORGANISM: Artificial Sequence
<220> FEATURE:
<223> OTHER INFORMATION: protein kinase A substrate

<400> SEQUENCE: 22

Leu Arg Arg Ala Ser Pro
 1               5

<210> SEQ ID NO 23
<211> LENGTH: 6
<212> TYPE: PRT
<213> ORGANISM: Artificial Sequence
<220> FEATURE:
<223> OTHER INFORMATION: protein kinase A substrate

<400> SEQUENCE: 23

Leu Arg Arg Ala Thr Pro
 1               5

<210> SEQ ID NO 24
<211> LENGTH: 7
<212> TYPE: PRT
<213> ORGANISM: Artificial Sequence
<220> FEATURE:

-continued

```
<223> OTHER INFORMATION: protein kinase A substrate

<400> SEQUENCE: 24

Arg Arg Ala Ser Phe Val Phe
1               5

<210> SEQ ID NO 25
<211> LENGTH: 7
<212> TYPE: PRT
<213> ORGANISM: Artificial Sequence
<220> FEATURE:
<223> OTHER INFORMATION: protein kinase A substrate

<400> SEQUENCE: 25

Arg Arg Ala Thr Phe Val Phe
1               5

<210> SEQ ID NO 26
<211> LENGTH: 4
<212> TYPE: PRT
<213> ORGANISM: Artificial Sequence
<220> FEATURE:
<223> OTHER INFORMATION: PKA substrate
<221> NAME/KEY: VARIANT
<222> LOCATION: (1)...(4)
<223> OTHER INFORMATION: Xaa = Any Amino Acid

<400> SEQUENCE: 26

Arg Arg Xaa Ser
1

<210> SEQ ID NO 27
<211> LENGTH: 4
<212> TYPE: PRT
<213> ORGANISM: Artificial Sequence
<220> FEATURE:
<223> OTHER INFORMATION: PKA substrate
<221> NAME/KEY: VARIANT
<222> LOCATION: (1)...(4)
<223> OTHER INFORMATION: Xaa = Any Amino Acid

<400> SEQUENCE: 27

Arg Arg Xaa Thr
1
```